US006800444B1

(12) United States Patent
Cook et al.

(10) Patent No.: US 6,800,444 B1
(45) **Date of Patent: *Oct. 5, 2004**

(54) COMPLEX CHEMICAL LIBRARIES

(75) Inventors: Phillip Dan Cook, Escondido, CA (US); Haoyun An, Encinitas, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/107,688

(22) Filed: Jun. 30, 1998

Related U.S. Application Data

(62) Division of application No. 08/744,020, filed on Nov. 5, 1996, now Pat. No. 5,780,241.

(51) Int. Cl.[7] .................... G01N 33/53

(52) U.S. Cl. .................... 435/7.1; 546/298

(58) Field of Search .................... 546/298; 435/7.1

(56) References Cited

U.S. PATENT DOCUMENTS

| | | | | |
|---|---|---|---|---|
| 5,010,175 A | | 4/1991 | Rutter et al. | 530/334 |
| 5,143,854 A | | 9/1992 | Pirrung et al. | 436/518 |
| 5,288,514 A | | 2/1994 | Ellman | 427/2 |
| 5,324,483 A | | 6/1994 | Cody et al. | 422/131 |
| 5,364,851 A | * | 11/1994 | Joran | 530/345 |
| 5,449,754 A | | 9/1995 | Nishioka | 530/334 |
| 5,472,672 A | | 12/1995 | Brennan | 422/131 |
| 5,489,678 A | | 2/1996 | Fodor et al. | 536/22.1 |
| 5,565,324 A | | 10/1996 | Still et al. | 435/6 |
| 5,646,285 A | * | 7/1997 | Baindur et al. | 546/298 |
| 5,780,241 A | | 7/1998 | Cook | 435/7.1 |

FOREIGN PATENT DOCUMENTS

| | | |
|---|---|---|
| WO | WO 92/20822 | 11/1992 |
| WO | WO 93/04204 | 3/1993 |
| WO | WO 93/20242 | 10/1993 |
| WO | WO 93/22678 | 11/1993 |
| WO | WO 94/08051 | 4/1994 |
| WO | WO 94/22454 | 10/1994 |
| WO | WO 94/24314 | 10/1994 |
| WO | WO 94/26775 | 11/1994 |
| WO | WO 94/27719 | 12/1994 |
| WO | WO 94/28080 | 12/1994 |
| WO | WO 94/28424 | 12/1994 |
| WO | WO 95/19567 | 7/1995 |
| WO | WO 96/30377 | 10/1996 |

OTHER PUBLICATIONS

Smith et al., Bioorganic and Medicinal Chemistry Letters, V.4, No. 24, 2821–2824, 1994.*

Cheng et al., J. Am. Chem. Soc., V.118, 2567–2573, Mar. 20, 1996.*

Boger et al., J. Am. CHem. Soc., V.118, 2109–2110, Feb. 28, 1996.*

Carell et al., Angew. Chem. Int. Ed. Engl., V.33, No. 20, 2059–2061, 1994.*

An et al., Tetrahedron Letters, V.37, No. 40, 7233–7236, Sep. 30, 1996.*

Ostresh et al., Proc. Nat. Acad. Sci. USA, V.91, 11138–11142, 1994.*

Gallop et al., Journal of Medicinal Chemistry, V.37, No. 9, 1233–1251, Apr. 29, 1994.*

Lebl et al., Biopolymers, V.37, 177–198, 1995.*

Achari et al., "Facing up to Membranes: Structure/Function Relationships in Phospholipases", *Cold Spring Harbor Symp. Quant. Biol.*, 1987, 52, 441–445.

Bomalaski et al., "Human extracellular recombinant phospholipase $A_2$ induces an inflammatory response in rabbit joints", *Immunol.*, 1991, 146, 3904–3910.

Burack et al., "Role of lateral phase separation in the modulation of phospholipase $A_2$ activity", *Biochemistry*, 1993, 32, 583–589.

Campbell et al., "Inhibition of Phospholipase $A_2$; a Molecular Recognition Study", *J. Chem. Soc., Chem. Commun.*, 1988, 1560–1562.

Carell et al., "A Novel Procedure for the Synthesis of Libraries Containing Small Organic Molecules", *J. Angew. Chem. Int. Ed. Engel.*, 1994, 33, 2059–2061.

Carell et al., "A Solution–Phase Screening Procedure for the Isolation of Active Compounds from a Library of Molecules", *J. Angew. Chem. Int. Ed. Engel.*, 1994, 33, 2061–2064.

Cho et al., "The Chemical Basis for Interfacial Activation of Monomeric Phospholipases $A_2$", *J. Biol. Chem.*, 1988, 263, 11237–11241.

Davidson et al., "1–Stearyl,2–Stearoylaminodeoxy Phosphatidylcholine, A Potent Reversible Inhibitor of Phospholipase $A_2$ ", *Biochem. Biophys. Res. Commun.*, 1986, 137, 587–592.

Davidson et al., "Inhibition of Phospholipase $A_2$ by "Lipocortins" and Calpactins", *J. Biol. Chem.*, 1987, 262, 1698–1705.

Debart et al., "Intermolecular Radical C–C Bond Formation: Synthesis of a Novel Dinucleoside Linker for Non–anionic Antisens Oligonucleosides", *Tetrahedron Lett.*, 1992, 33, 2645–2648.

Dennis, E.A., "Phospholipase", The Enzymes, vol. 16, Chapter 9, pp. 307–353, Boyer, P.D., Ed., Academic Press, New York, 1983.

(List continued on next page.)

*Primary Examiner*—Bennett Celsa
(74) *Attorney, Agent, or Firm*—Woodcock Washburn LLP

(57) ABSTRACT

Compositions comprising novel chemical libraries are prepared. The compositions of the present invention are useful as antibacterial and other pharmaceutical agents and as intermediates for preparation of other pharmaceutical agents. In addition, compounds of the present invention are useful as research reagents.

7 Claims, 3 Drawing Sheets

OTHER PUBLICATIONS

DeWitt et al., "Diversomers": An approach to nonpeptide, nonoligomeric chemical diversity, *Proc. Natl. Acad. Sci. USA*, 1993, 90, 6909–6913.
Ecker et al., "Rational Screening of Oligonucleotide Combinatorial Libraries for Drug Discovery", *Nucleic Acids Res.*, 1993, 21(8), 1853–1856.
Essien H., "Synthesis of Diethylenetriaminepentaacetic Acid Conjugated Inulin and Utility for Cellular Uptake of Liposomes", *J. Med. Chem.*, 1988, 31, 898–901.
Franson et al., "Phospholipid Metabolism by Phagocytic Cells. Phospholipases $A_2$ Associated with Rabit Polymorphonuclear Leukocyte Granules", *J. Lipid Res.*, 1974, 15, 380–388.
Gallop, M.A. et al., "Applications of Combinatorial Technologies to Drug Discovery. 1. Background and Peptide Combinatorial Libraries", *J. Med. Chem.*, 1994, 37, 1233–1251.
Geysen et al., "Strategies for epitope analysis using peptide synthesis", *J. Immun. Meth.*, 1987, 102, 259–274.
Giannis et al., "Fragmentation and Wittig Olefination of Glucosamine Derivatives–a Simple Route to Open Chain Amino Sugars and Chiral Glycerols", *Tetrahedron*, 1988, 44, 7177–7180.
Glaser et al., "Phospholipase $A_2$ enzymes: regulation and inhibition", *TIPS Reviews*, 1992, 14, 92–98.
Grainger et al., "An enzyme caught in action: direct imaging of hydrolytic function and domain formation of phospholipase $A_2$ in phosphatidylcholine monolayers", *FEBS*, 1989, 252, 73–82.
Houghten et al., "Generation and Use of Synthetic Peptide Combinatorial Libraries for Basic Research and Drug Discovery", *Nature*, 1991, 354, 84–86.
Lebl, M. et al., "One–Bead–One–Structure Conbinatorial Libraries", *Biopolymers Peptide Sci.*, 1995, 37, 177–198.
Lombardo et al., "Cobra Venom Phospholipase $A_2$ Inhibition by Manoalide", *J. Biol. Chem., 260*, 1985, 7234–7240.
Marki et al., "Differential inhibition of human scretary and cytosolic phospholipase $A_2$", *Agents Actions*, 1993, 38, 202–211.
Miyake et al., "The Novel Natural Product YM–26567–1 [(+)–trans–4–(3–dodecanoyl–2,4, 6–trihydroxyphenyl)–7–hydroxy–2–(4–hydroxyphenyl) chroman]: A Competitive Inhibitor of Group II Phospholipase $A_2$", *J. Pharmacol. Exp. Ther.*, 1992, 263, 1302–1307.
Ohlmeyer et al., "Complex synthetic chemical libraries indexed with molecular tags", *Proc. Natl. Acad. Sci. USA*, 1993, 90, 10922–10926.
Oinuma et al., "Synthesis and biological evaluation of substituted benzenesulfonamides as novel potent membrane–bound phospholipase $A_2$ inhibitors", *J. Med. Chem.*, 1991, 34, 2260–2267.
Ostresh, J.M. et al., "'Libraries from libraries': Chemical transformation of combinatorial libraries to extend the range and repertoire of chemical diversity", *Proc. Natl. Acad. Sci.*, 1994, 91, 11138–11142.
Owens et al., "The Rapid Identification of HIV Protease Inhibitors Through the Synthesis and Screening of Defined Peptide Mixtures", *Biochem. & Biophys. Res.*, 1991, 181, 402–408.
Noel et al., "Phospholipase $A_2$ Engineering. 3. Rerplacement of Lysine–56 by Neutral Residues Improves Catalytic Potency Significantly, Alters Substrate Specificity, and Clarifies the Mechanism of Interfacial Recognition", *J. Am. Chem. Soc.*, 1990, 112, 3704–3707.
Sampson et al., "Identification and Characterization of a New Gene of *Escherichia coli* K–12 Involved in Outer Membrane Permeability", *Genetics*, 1989, 122, 491–501.
Scott et al., "Interfacial Catalysis: The Mechanism of Phospholipase $A_2$", *Science*, 1990, 250, 1541–1546.
Simon et al., "Peptoids: A modular approach to drug discovery", *Proc. Natl. Acad. Sci. USA*, 1992, 89, 9367–9371.
Tanaka et al., "A Novel Type of Phosopholipase $A_2$ Inhibitor, Theielocin A1β, and Mechanism of Action", *J. Antibiotics*, 1992, 45, 1071–1078.
Vishwanath et al., "Edema–Inducing Activity of phospholipase $A_2$ Purified from Human Synovial Fluid and Inhibition by Aristolochic Acid", *Inflammation*, 1988, 12, 549–561.
Vloon et al., "Synthesis and Biological Properties of Side–Chain–Modified Bleomycins", *J. Med. Chem.*, 1987, 30, 20–24.
Washburn et al., "Suicide–inhibitory Bifunctionally Linked Substrates (SIBLINKS) as Phospholipase $A_2$ Inhibitors", *J. Biol. Chem.*, 1991, 266, 5042–5048.
Wery et al., "Structure of recombinant human rheumatoid arthiritic synovial fluid phospholipase $A_2$ at 2.2A resolution", *Nature*, 1991, 352, 79–82.
Wyatt et al., "Combinatorially selected guanosine–quartet structure is a potent inhibitor of human immunodeficiency virus enveloped–mediated cell fusion", *Proc. Natl. Acad. Sci., USA*, 1994, 91, 1356–1360.
Yang et al., "Studies on the status of lysine residues in phospholipase $A_2$ from *Naja naja atra* (Taiwan cobra) snake venom", *Biochem. J.*, 1989, 262, 855–860.
Yuan et al., "Synthesis of Some 2–Substituted Aminobenzothiazoles", *Beijing Daxue Xuebao, Ziran Kexueban*, 1988, 24, 504–506.
Yuan et al., "Synthesis and Evaluation of Phospholipid Analogues as Inhibitors of Cobra Venom Phospholipase $A_2$", *J. Am. Chem. Soc.*, 1987, 109, 8071–8081.
Zuckermann et al., "Efficient Method for the Preparation of Peptoids [Oligo(N–substituted glycines)] by Submonomer Solid–Phase Synthesis", *J. Am. Chem. Soc.*, 1992, 114, 10646–10647.
Pruzanski et al., "Enzymatic Activity and Immunoreactivity of Extracellular Phospholipase $A_2$ in Inflammtory Synovial Fluids", *Inflammation*, 1992, 16, 451–457.

* cited by examiner

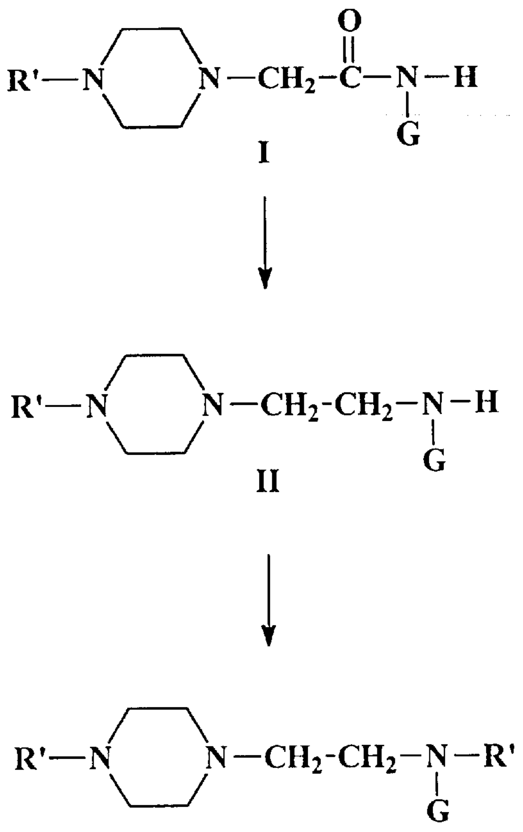
I: G = A, Library 3, B, Library 4
II: G = A, Library 9, B, Library 10
III: G = A, Library 19 B, Library 11
R' = benzyl, 2-methylbenzyl, 2-nitrobenzyl, 2-fluorobenzyl, 2-trifluoromethylbenzyl, 2-cyanobenzyl, or 2-methoxycarbonylbenzyl
G =
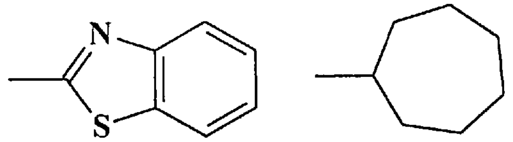
A B
Figure 1

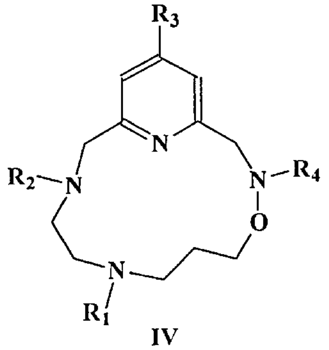

$R_1, R_2, R_5$ = benzyl, 3-fluorobenzyl, 2-xylene, (3-methoxycarbonyl)benzyl, 3-nitrobenzyl, or 2-trifluoromethylbenzyl.

IV

R3 = H, R4 = t-Boc, Library 21

R3 = 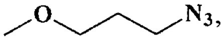 $N_3$, R4 = t-Boc, Library 26

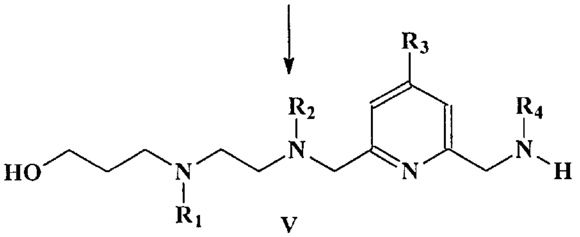

V

R3 = H, R4 = t-Boc, Library 22

R3 = 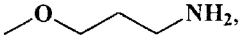 $NH_2$, R4 = t-Boc, Library 27

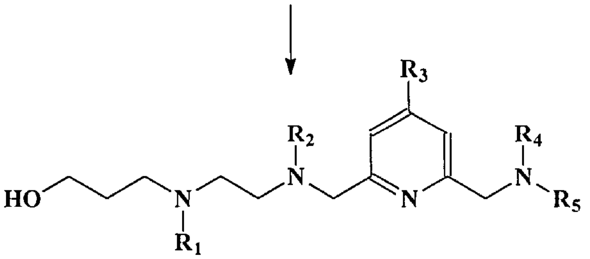

VI

R3 = H,

R4 = t-Boc, Library 23

R4 = H, Library 24

R4 = benzyl, 3-fluorobenzyl, 2-xylene, (3-methoxycarbonyl)benzyl, 3-nitrobenzyl, or 2-trifluoromethylbenzyl, Library 25

R3 = 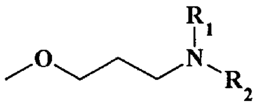

R4 = t-Boc, Library 28

R4 = H, Library 29

R4 = benzyl, 3-fluorobenzyl, 2-xylene, (3-methoxycarbonyl)benzyl, 3-nitrobenzyl, or 2-trifluoromethylbenzyl, Library 30

Figure 2

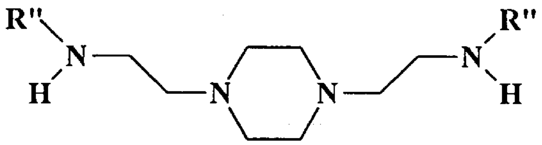
VII
Library 17
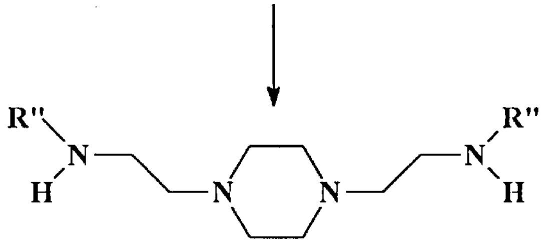
VIII
Library 18
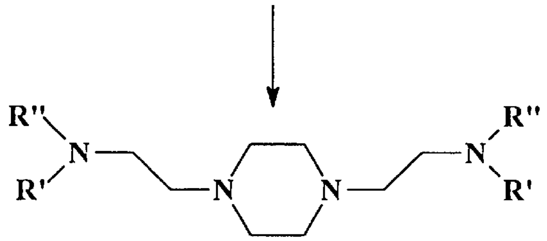
IX
Library 20
R' = benzyl, 2-methylbenzyl, 2-nitrobenzyl, 2-fluorobenzyl, 2-cyanobenzyl, 2-trifluoromethylbenzyl, or 2-methoxycarbonylbenzyl
R'' = 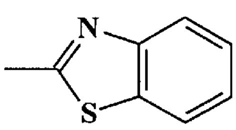 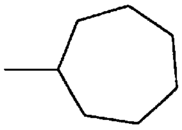 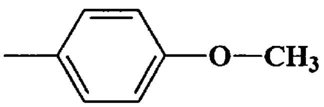
Figure 3

COMPLEX CHEMICAL LIBRARIES

CROSS REFERENCE TO RELATED APPLICATIONS

This application is a divisional of U.S. Ser. No. 08/744,020, filed Nov. 5, 1996, now U.S. Pat. No. 5,780,241.

FIELD OF THE INVENTION

The present invention is directed to methods for the preparation of complex chemical libraries to libraries thus prepared and to methods for their employment as pharmaceuticals and pharmaceutical building blocks. Pharmaceutical activity has been shown for libraries prepared in accordance with the present invention. The present compositions are also useful as chemical reagents, having commercial significance, utility and value per se.

BACKGROUND OF THE INVENTION

From the discovery of penicillin by Fleming in 1940's there has been a constant search for new antibiotics, which search continues to this day. Although many antibiotics have been discovered, there is an on-going need for the discovery of new antibiotic compounds because of the emergence of drug resistant strains of bacteria. Thus, research on bacterial infection is a perpetual cycle of development of new antibiotics. When penicillin was first discovered, its broad-spectrum antibiotic activity was hailed as the "magic bullet" in fighting many bacterial infections. However, over the years, many strains of bacteria have developed a resistance to penicillin and other currently available antibiotic drugs. No antibiotic drug is effective against all bacterial infections. Many antibiotic drugs available today have narrow-spectrum of activity, that is, they are effective against only few specific types of bacterial infections. Thus, for example, the majority of current antibiotic drugs are ineffective against syphilis and tuberculosis. In addition, some strains of syphilis, tuberculosis and other bacteria have developed resistance to currently available antibiotic drugs, which were effective drugs in the past.

Most bacteria which are resistant to a given drug also exhibit similar resistance to chemically similar drugs. Currently, many antibiotics are based on the β-lactam chemical core structure of penicillin. Although other chemically diverse antibiotics, such as vancomycin, are currently available, it is only a matter of time before the emergence of bacterial strains which will be resistant to all currently available antibiotic drugs. Thus, to prevent a future worldwide epidemic of drug resistant bacterial infections, there is a never ending need for a development of antibiotic drugs with novel chemical structures. This invention addresses this goal among others.

It is, accordingly, an object of this invention to provide novel processes for the preparation of compositions of compounds for use as antibiotics and other pharmaceuticals.

A further object of the invention is to provide products produced by processes herein disclosed for the preparation of pharmaceuticals and other useful chemical species.

Another object of the present invention is to provide complex chemical libraries which are useful, per se as antibiotics, and as other pharmaceutical formulations, as well as research reagents.

A further object of the invention is to provide methods for the creation of complex chemical libraries and for the attainment of increased complexity (albeit complexity following logical, preselected paradigms) in pre-existing chemical libraries.

Yet another object is to provide methods for the identification of useful drugs and reagents.

These and other objects will become apparent to persons of ordinary skill in the art from a review of the present specification and appended claims.

SUMMARY OF THE INVENTION

The present invention is directed to methods for preparing chemical libraries and to the useful libraries thus formed. Chemical libraries are known per se for use in the preparation of pharmaceuticals, as research reagents, and as intermediates in the preparation of other useful chemical species. Chemical libraries are commercial products per se and are useful commodities in and of themselves. It has now been found that certain chemical libraries have pharmaceutical use in themselves, exhibiting antibacterial activity and activity in certain other biological assays.

In accordance with the present invention, improved chemical libraries are prepared by reacting a mixture of at least four reactive chemical compounds with a chemical scaffold moiety. This reaction provides a mixture of reaction products. Following such reaction, the scaffold moiety portion of those reaction products is transformed so as to alter either its chemical properties, its electrochemical properties, or both. This transformation of the scaffold moiety portion of the reaction products is accomplished either by the opening of a chemical ring comprising the scaffold, by cyclization of a portion of the scaffold, by appending to the scaffold at least one chemical substituent, or by certain other chemical reactions. Exemplary of such additional reactions is the alteration of the oxidation state of one or more functionalities on the scaffold, alkylation of the scaffold, or acylation of the scaffold. Other chemical, electrochemical, or other reactions which can give rise to alterations in the scaffold can also be used if the scaffold's chemical or electrochemical properties are changed thereby.

In accordance with certain preferred embodiments, the scaffolds are electrochemically or chemically reduced such as to effect the reduction of a carbonyl moiety, unsaturation or the like. Ring opening reactions are also preferred for use in accordance with the present invention, especially when such rings comprise a macrocycle. It is convenient to employ macrocycles having at least one nitrogen-oxygen bond, since the same are quite labile towards ring opening. Other ring opening reactions may also be used, however.

Other transformations which are within the present invention include nucleophilic substitutions involving the scaffold moieties, especially nucleophilic substitutions involving nitrogen. In accordance with other preferred embodiments, nucleophilic or other substitutions on the scaffold are employed in such a fashion that additional reactive moieties are added thereto. Exemplary additional reactive moieties are amido, imino, and primary and secondary nitrogen functions. It will be appreciated that these functions are capable of further reaction to provide further diversity in chemical libraries in accordance with the present invention.

In accordance with other preferred embodiments of the present invention, the transformed scaffold moiety portions of the mixture of reaction products are reacted with a set of at least four reactive chemical moieties to form a further library of chemical compounds.

It is convenient to perform the methods of the present invention in an iterative fashion whereby an original scaffold moiety is sequentially and repeatedly altered or transformed and then reacted with sets of chemical reactant species to form very complex chemical libraries. The present invention is also directed to chemical libraries prepared in accordance with the methods of the present invention. The libraries have been found to have antibacterial and activity such that antibacterial compositions comprising chemical libraries prepared in accordance with the present invention are provided. Other pharmaceutical utility exists for the compositions of the invention including antifungal, biological inhibitory and other properties.

BRIEF DESCRIPTION OF THE DRAWINGS:

FIG. 1 depicts a reaction scheme for transforming a scaffold which has been reacted with a set of chemical reactive functionalities, following by subsequent reaction with a further set of chemical reactive functionalities to form libraries.

FIG. 2 depicts a transformation of a scaffold moiety through ring opening with subsequent reaction of the ring-opened species with sets of chemical reactants.

FIG. 3 depicts substitution reactions on a scaffold species to effect transformation thereof and the preparation of and soon, complex libraries of chemical compounds.

DETAILED DESCRIPTION OF PREFERRED EMBODIMENTS

In accordance with the present invention, chemical libraries are prepared. A mixture of at least four chemical reactive compounds are reacted with a scaffold moiety to provide a mixture of reaction products. The scaffold moiety portions of the reaction products are then transformed to alter the chemical or electrochemical properties of the scaffold. The libraries ensues.

Respecting certain preferred aspects of the present invention, the transformation of the scaffold moiety portions takes place through opening of the chemical ring comprising the scaffold, by cyclization of a portion of the scaffold, by appending to the scaffold at least one chemical substituent, by alteration of the oxidation state of at least one functionality on the scaffold, by alkylation of the scaffold, or by acylation thereof. Combinations of the foregoing reactions may also be employed to affect transformation of the scaffold moiety portions.

Following transformation of the scaffold moiety portions, the mixture of reaction products may then be reacted with a further set of reactive chemical species to give rise to a complex chemical library. It is also within the spirit of the invention to transform the scaffold portion of the resulting mixture in such a way as to alter the chemical or electrochemical properties thereof and give rise to still further libraries of chemical compounds either through further reaction with sets of reactants or otherwise.

Scaffold moieties can then be reacted with sets or mixtures of chemical reactive compounds. In this context, the chemical reactive compounds and the scaffold moieties are best defined by reference to each other and by the reactions in which they participate. Accordingly, as will be appreciated by persons of ordinary skill in the art, chemical reactive compounds are those compounds which are capable of reacting with scaffold moieties in a combinatorial fashion. Thus, such chemical reactive compounds generally share certain qualities, functionalities, or structures so as to permit them to react with a putative scaffold moiety at a common reaction situs and in a generally common fashion such as via an Sn-2 reaction mechanism or the like.

For example, a mixture of benzyl halides such as benzyl, 2-methylbenzyl, 2-nitrobenzyl, 2-fluorobenzyl, 2-cyanobenzyl, 2-triflouromethylbenzyl, and 2-methoxy carbonylbenzyl halides, e.g. bromides, can form a convenient mixture of chemical reactive compounds in accordance with this invention. As will be appreciated by persons skilled in the art, the forgoing benzylic compounds are all amenable to nucleophilic substitution at the benzylic position. Large varieties of other chemical reactant species and sets thereof will be readily apparent to persons of ordinary skill in the art. For example, a set of alpha haloketo compounds can easily be prepared from commercially available materials. Indeed, many such chemical reactants are available commercially and can easily be blended. The chemical reactive compounds may be such as to be reactive with the scaffold moieties to any of the chemical reactions which are presently known or may be discovered heretofore. Thus, nucleophilic or other substitution, electrophilic reaction, cyclization, addition, and other reactions may be participated in between the scaffold molecules of the present invention and the chemical reactive species. It will, accordingly, be understood that the precise identity of the chemical reactant species was not limiting in the present invention, but that all such species which are capable of reacting with scaffold molecules, are contemplated hereby.

The scaffold moieties of the present invention are, similarly, best defined by their chemical relationship to the chemical reactant species. Thus, such scaffolds are capable of reacting with one or more sets of chemical reactant species, preferably a plurality thereof. For example, in dealing with a set of benzylic halides as discussed hereinabove, it is convenient that the scaffold moieties comprise at least one nitrogenous species, preferably a primary or secondary amine, which is capable of nucleophilic displacement of the halide function at the benzylic position of the chemical reactant species. In accordance with preferred embodiments, the scaffold moieties of the present invention have pluralities of functionalities such that they may participate in reaction with chemical reactant compounds at a number of locations to give rise to complex chemical libraries. It is also generally necessary in accordance with the invention that the scaffold molecules have at least one chemical functionality which is capable of undergoing a transformation of its chemical or electrochemical properties. Accordingly, it is preferred that the scaffold moieties be capable of undergoing ring opening, ring contraction, cyclization, substitution by at least one chemical substituent, or certain other reactions. It is also within the spirit of the present invention that the scaffold moieties be capable of undergoing a change in oxidation state of at least one functionality thereupon, or alkylation, acylation, and the like.

It is preferred that the scaffold moieties be selected as to be able to react with an initial set of chemical reactant compounds to form a mixture of reaction products. The scaffold moiety portion of such products are then caused to be transformed so as to change either their chemical or electrochemical properties. The transformed set of reaction products is, itself, a chemical library having potential utility. Significantly, however, this transformed library may also be caused to undergo reaction with a further set of chemical reactant species to form even greater complexity in the ensuing chemical libraries. As will be appreciated, subsequent transformation of the scaffold portion may be caused to occur either with or without subsequent reaction with additional sets of chemical reactant species to give rise to chemical libraries having great complexity.

The individual reactions useful in the preparation of chemical modifications in accordance with the present invention are well known to organic chemists and others skilled in the organic chemistry art. Thus, reaction conditions, solvents, temperatures, and other parameters for substitution reactions, changes in oxidation state, acylations, ring openings, ring closings and the other transformative reactions as may be used in connection with the present invention are not, in and of themselves, part of the present invention. Rather, the foregoing reactions, and others as will occur to the routineer, will be employed to achieve the objectives of the present invention. The present application sets forth numerous examples depicting the transformation reactions useful for changing the chemical or electrochemical properties of scaffold moieties. Others will be apparent to those skilled in the art.

The term "to change the chemical or electrochemical properties" as applied to the scaffold molecules or moieties of the present invention should be understood by persons skilled in the art. In effecting the transformation of a scaffold moiety, either its chemical properties, e.g., its reactivity, size, structure, functionality, or ability to interact with its environment, such as biological systems and the like, is changed. The change in the oxidation state of scaffold moieties, as exemplified by the reduction of amide functionalities, (reduction) or the elimination of a hydroxyl or other leaving group through an E-2 or other elimination reaction (oxidation) are contemplated hereby. The change in oxidation state of scaffold moieties allows the introduction and removal of differing functional groups from the developing chemical libraries and permits the attainment of increasing diversity therein.

By reacting an initial scaffold moiety with a set of reactive chemical functionalities, followed by either an oxidation or reduction (or other chemical or electrochemical transformation), a new set of molecules result which can be subsequently processed to increase chemical diversity. Accordingly, such groups of reactive molecules are again either oxidized, reduced, substituted, cyclized, ring-opened, etc. to give rise to scaffolds moiety portions which are able to undergo additional, new or different reactions with further sets of chemical reactant species. Perforce, the iterative employment of reaction with a group of chemical reactive species followed by transformation, followed by further reaction with a group of chemical species gives rise to very complex chemical libraries.

Such complexity, however, is not illogical or completely random. By knowing the identity of the chemical reactants, the order of reaction, the nature of the transformation of the scaffold moieties, and the relative reactivity of the various species, it is possible to engineer or design chemical libraries having precise, component, chemical compounds. Thus, it is possible to develop chemical libraries of dozens, hundreds, and even many thousands of chemical compounds, all of which, however, are known to the preparer. This being the case, it is possible to use these libraries either per se, such as an antibiotic or the like, or as a chemical intermediates to the preparation or identification of pharmaceuticals or other useful species. As is known, such libraries are articles of commerce, themselves, without further modification, and, as such, have utility. Accordingly, the ability to prepare such complex libraries in a reliable, predictable, and stoichiometric fashion is highly desired.

In accordance with a further embodiment of the present invention, relatively equimolar amounts of the chemical components of the chemical libraries can be attained. This is done through normalization of the sets of chemical reactant species in view of their relative reactivity towards the functional group or groups of a particular scaffold molecule or moiety. In this respect, the chemical reactant species are assessed in terms of their reactivity and their relative respective composition is altered in inverse proportion to that reactivity such that, following reaction with the scaffold, relatively equal molar products are formed.

In accordance with preferred embodiments of this invention, compositions are provided which comprise mixtures of compounds. It has been found that such compositions have antibacterial activity, in some cases against both Gram negative and Gram positive bacteria.

Compositions comprising compounds disclosed herein are useful as antibiotics as well as in other therapeutic areas including treatment of fungal infections, viral infections, various type of neoplastic disease, cardiovascular diseases, central nervous system disorders, inflammation and immune disorders. Compositions of the present invention can inhibit both Gram positive bacteria, exemplified by *Escherichia Coli* (*E. Coli*), and Gram negative bacteria, such as *Streptococcus Pyogenes* (*S. Pyogenes*). Accordingly, the present invention provides therapeutic regimes against bacterial infection employing compositions set forth herein. In addition to antibiotic activities, compounds of the present invention are useful in other pharmaceutical areas and as intermediates for preparation and discovery of pharmaceutically active agents. The compositions of the invention which utilize nitrogen heterocycles as a common scaffold (as illustrated in the examples) are likely to be useful in a number of therapeutic arenas, including muscle relaxants (as, for example, pipercurium bromide), anthelminthic drugs (as, for example, piperazine and its analogues), antineoplastic agents (as, for example, piposulfan), biological buffers (as, for example, piperazine derivatives such as piperazinediethanesulfonic acid), anti-ulcerative agents (as, for example, pirenzepine), antihypertensive agents (as, for example, prazosin), and anti-inflammatory agents (as, for example, protacine (proglumetacin)). Compositions of the present invention can also be used in or as an intermediate for preparing or discovering drugs useful in the treatment of neoplastic diseases, immune disorders, cardiovascular diseases, central nervous system disorders and inflammation, among others.

For pharmaceutical use, it is well within the knowledge of those skilled in the art to ascertain routes of drug administration and dosage levels for particular compounds that are obtained from compositions of the invention in view of the objects thereby to be attained. Thus, the dosage forms of the present invention can be administered orally, rectally, parenterally, or transdermally, alone or in combination with other psycho stimulants, antidepressants, and the like to a patient in need of treatment. Oral dosage forms include tablets, capsules, dragees, and other conventional, pharmaceutical forms. Isotonic saline solutions, conveniently containing about 1–200 milligrams of drug per milliliter can be used for parenteral administration which includes intramuscular, intrathecal, intravenous and intra-arterial routes. Rectal administration can conveniently be effected through the use of suppositories such as can easily be formulated from conventional carriers such as cocoa butter. Transdermal administration can be effected through the use of transdermal patch delivery systems and the like. The preferred routes of administration are oral and parenteral.

The dosage employed should be carefully titrated to the patient, considering age, weight, severity of the condition, and clinical-profile. The actual decision as to dosage will depend upon the exact drug being employed and will be made by the attending physician as a matter of routine. Such physician can, however, determine an appropriate regime employing well-known medical considerations. Unit dosage forms are selected as a matter of routine depending upon the selected route of administration. For oral administration, formulation into tablets using tableting excipients are conveniently employed, although capsular and other oral forms are also useful.

The terms "pharmaceutical", "pharmaceutically active" and "pharmaceutically useful" are used interchangeably herein and refer to ability of the compounds of the present invention to provide some therapeutic or physiological beneficial, effect. As used herein, the terms include any physiologically or pharmacologically activity that produces a localized or systemic effect or effects in animals, including warm blooded mammals such as humans. Pharmaceutically active agents may act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocoid systems, the alimentary and excretory systems, the histamine system and central nervous systems as well as other biological systems. Thus, compounds derived from compositions of the present invention may be used as sedatives, psychic energizers, tranquilizers, anticonvulsants, muscle relaxants, anti-Parkinson agents, analgesics, antiinflammatories, local anesthetics, muscle contractants, antibiotic, antiviral, antiretroviral, antimalarials, diuretics, lipid regulating agents, antiandrogenic agents, antiparasitics, neoplastics, antineoplastics and chemotherapy agents. These compounds could further be used to treat cardiovascular diseases, central nervous system diseases, cancer, metabolic disorders, infections and dermatological diseases as well as other biological disorders and infections.

Among the uses of the compositions and compounds of the present invention are uses in scientific research as research reagents. In accordance with the present invention, it is now possible to prepare pluralities of compounds in accordance with the invention to form a composition of matter in the nature of a "library" of compounds for research. Such libraries are known to be useful, per se and are important in the discovery, inter alia, of new drugs. In view of the chemical diversity present in such compounds, e.g. the large number of functional groups and functionalizable sites, a very large number of different compounds can be prepared. Moreover, such compounds can be prepared differentially, that is, in such a fashion that a population of known species can be prepared reliably, ensuring that all potential members of a family of chemical species are, in fact, synthesized.

In view of the foregoing, persons of ordinary skill in the art will know how to synthesize such libraries, comprising chemical compositions within the scope and spirit of this invention, and to assay the libraries against etiological agents or in tests or assays, in order to identify compounds having antibacterial, antifungal, antiviral, antineoplastic or other desired pharmaceutical, biological, or chemical activity.

For example, compositions of the present invention may be used in any of the many combinatorial drug identification methodologies known to persons skilled in the art of subsequently developed. Exemplary uses of this type are those described in Fodor et al., U.S. Pat. No. 5,489,678; Pirrung et al. U.S. Pat. No. 5,143,854; Lerner et al., PCT patent application WO 93/20242; Lebl et al. PCT patent application WO 94/28028; Hollis et al. PCT patent application WO 93/22678; Brennan U.S. Pat. No. 5,472,672, Nishioka U.S. Pat. No. 5,449,754 and Ecker et al., PCT patent application WO 93/04204.

As will be readily apparent to persons of skill in the art from a review of the present specification, useful compositions can be obtained by preparing mixtures of compounds formed from the constituent moieties forming the present compounds. Thus, compounds formed by reacting sets chemically reactive compounds, such as meta benzylic compounds, alpha-amide compounds or other compounds having a reactive group thereupon, with one or a family of scaffold molecules having a plurality of reactive functionalities thereupon, have great utility as pharmaceuticals.

For meta benzyl compounds, it is preferred that the reactive functions reside on the benzylic carbon atom and that the same comprise a leaving group. For the alpha-amides, which are also preferred, the reactive functional group is also a leaving group, but may conveniently reside alpha to the carbonyl. Preferably, the leaving group is a halogen, such that the groups are alpha haloamides. Other chemically reactive chemical species having a wide variety of functional groups thereupon may be employed in accordance with the spirit of this invention.

Preferred scaffold molecules are those which possess, at least two functional groups, at least one of which can react with reactive compounds e.g. appendage molecules. It is preferred that two or more functional groups be present such that great diversity of resulting species can be attained. Thus, scaffolds having two, three and more functional groups reactive with appendage molecules, either in the same chemical way or in different ways, are highly useful in the practice of this invention. One preferred scaffold species are di-nitrogen heterocycles as illustrated in the examples and disclosed in U.S. patent application No. 691,149, entitled Di-Nitrogen Heterocycle Compositions, filed Aug. 1, 1996. Another preferred scaffold specie is the macrocyclic compounds as illustrated in the examples and disclosed in PCT/US96/04215, filed Mar. 27, 1996, entitled Macrocyclic Compounds Having Nitrogen-Containing Linkages and further identified by attorney docket No. Many other scaffold species can be used, however.

It is preferred to react a plurality of chemically reactive compounds with the scaffold molecules and also, in some preferred cases, to provide a plurality of scaffold molecules for such reactions. The resulting compositions can be seen to be mixtures of reaction species. One preferred use for such mixtures is in the identification of chemical species which have biological activity, especially pharmaceutical activity. Such mixtures can be screened for activity and active molecular species determined. Such mixtures, conventionally denominated "libraries" are useful per se, and are well known to be useful in the chemical and pharmaceutical industry, where the preparation and exchange of libraries for screening is a common undertaking.

Compositions of the invention can be deconvoluted to single active molecular species utilizing deconvolution methods and techniques known to those skilled in the art. "Deconvolution" is construed to mean taking the totality of a population and systematically working through that population to establish the identity of a particular member, selected members, or all members of the population. In deconvoluting a combinatorial library of compounds, systematic selection is practiced until an individual compound or a group of individual compounds having a particular characteristic, as for instance being an active species in a specific functional assay, is identified.

There are many strategies for the deconvolution of combinatorial libraries including iterative processes of splitting and fixing one position and subtractive techniques where selected letters are removed from selected pools and the active pools are pursued to elicit the most active compound. Other methods known in the art include labeling (including chemically or radioisotopically), enzyme binding assays, and selection assays. Another method involves fixing one letter at a time. A further method involves the use of protecting groups to make selected sites unavailable for functionalization until other sites are functionalized. Many of these methods can be combined to customize conditions to meet synthetic needs.

In order to maximize the advantages of each classical approach, new strategies for combinatorial deconvolution have been developed independently by several groups. Selection techniques have been used with libraries of peptides (Geysen, H. M., Rodda, S. J., Mason, T. J., Tribbick, G. and Schoofs, P. G., J. *Immun. Meth.* 1987, 102, 259–274; Houghten, R. A., Pinilla, C., Blondelle, S. E., Appel, J. R., Dooley, C. T. and Cuervo, J. H., *Nature*, 1991, 354, 84–86; Owens, R. A., Gesellchen, P. D., Houchins, B. J. and DiMarchi, R. D., *Biochem. Biophys. Res. Commun.*, 1991, 181, 402–408; Doyle, M. V., PCT WO 94/28424; Brennan, T. M., PCT WO 94/27719); nucleic acids (Wyatt, J. R., et al., *Proc. Natl. Acad. Sci. USA*, 1994, 91, 1356–1360; Ecker, D. J., Vickers, T. A., Hanecak, R., Driver, V. and Anderson, K., *Nucleic Acids Res.*, 1993, 21, 1853–1856); nonpeptides and small molecules (Simon, R. J., et al., *Proc. Natl. Acad. Sci. USA*, 1992, 89, 9367–9371; Zuckermann, R. N., et al., *J. Amer. Chem. Soc.*, 1992, 114, 10646–10647; Bartlett, Santi, Simon, PCT WO91/19735; Ohlmeyer, M. H., et al., *Proc. Natl. Acad. Sci. USA*, 1993, 90, 10922–10926; DeWitt, S. H., Kiely, J. S., Stankovic, C. J., Schroeder, M. C. Reynolds Cody, D. M. and Pavia, M. R., *Proc. Natl. Acad. Sci. USA*, 1993, 90, 6909–6913; Cody et al., U.S. Pat. No. 5,324,483; Houghten et al., PCT WO 94/26775; Ellman, U.S. Pat. No. 5,288,514, Still et al., PCT WO 94/0805; Kauffman et al., PCT-WO 94/24314; Carell, T., Wintner, D. A., Bashir-Hashemi, A. and Rebek, *J., Angew. Chem. Int. Ed. Engel.*, 1994, 33, 2059–2061; Carell, T., Wintner, D. A. and Rebek, J., *Angew. Chem. Int. Ed. Engel.*, 1994, 33, 2061–2064; Lebl, et al., PCT WO 94/28028). We have developed certain nitrogen coupled chemistries that we utilized to prepare a class of compounds we refer to as "oligonucleosides." We have described these compounds in.previous patent applications including published PCT applications WO 92/20822 (PCT US92/04294) and WO 94/22454 (PCT US94/03313). These chemistries included amine linkages, hydroxylamine linkages, hydrazino linkages and other nitrogen based linkages.

As illustrated in Examples 6, 13, 14 and Procedure 2, processes of the present invention have been useful to enhance the activity of a library of compounds. The Library prepared in Example 6 was found to have activity in Procedure 2 against *S. pyrogenes* and *E. coli*. This Library was reduced as per Example 13 and further treated with a selected group of reactant compounds as per Example 16 thereby increasing the complexity of the initial library. The final library shows enhanced activity in the assays against the bacterial agents *S. pyrogenes* and *E. coli.*

In general compositions prepared by processes of the present invention will be more diverse as well as more complex when compared to the initial compositions. The overall extent of diversification will be a factor of both the number of sites and the number of reactant species presented to each site for covalent bonding to the site. The complexity of the library is represented by the number of chemical functional groups taken to the power represented by the number of sites these chemical functional groups can be located at. Thus for example, 5 chemical functional groups at three unique sites will give a library of 125 ($5^3$) compounds, 20 chemical functional groups at 4 sites will give a library of 160,000 ($20^4$) compounds and 8 chemical functional groups at 6 sites will give a library of 262,144 ($8^6$) compounds.

The present invention is exemplified, in part, through the following examples. Such examples are to be deemed illustrative only and not as limiting the invention in any way.

EXAMPLES

In the following examples THF refers to tetrahydrofuran and DMF refers to dimethylformamide. 2-Mercapto-1-ethanesulfonic acid (sodium salt), 3-mercapto-1-propanesulfonic acid (sodium salt), 1-phenylpiperazine, THF, DMF, diisopropylethylamine, and 2-aminoethanesulfonic acid were purchased from Aldrich (Milwaukee, Wis.), 2-aminobenzothiazole was purchased from Lancaster (Windham, N.H.), and bromoacetyl bromide was purchased from Fluka (Ronkonkoma, N.Y.). Rotary evaporations were performed in vacuo (50 torr) at 35° C. unless otherwise noted. NMR was performed on a Varian Geminii 200 or Varian Unity 400. Mass spectrometry were taken on a Hewlett Packard 59987A electrospray mass spectrometer (quadrupole mass analyzer 0–2600 amu).

In the following examples, R' represents a mixture of the following substituents:

R' =

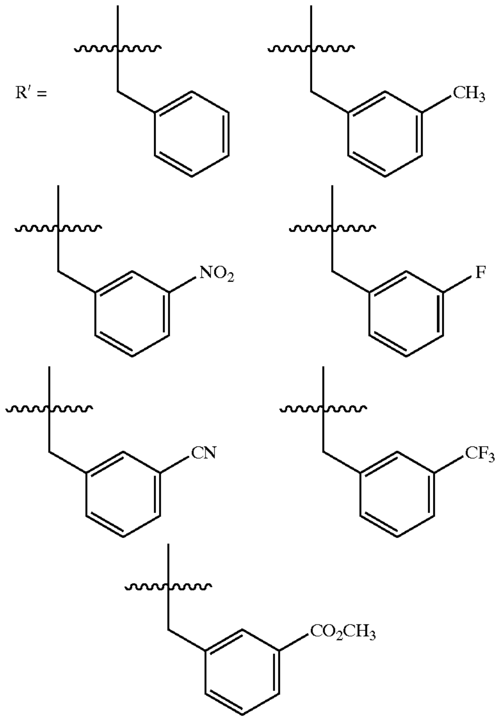

In the examples, $L_1$-$L_6$ represents the following substituents:

| | |
|---|---|
| $L_1$ | benzyl |
| $L_2$ | 3-fluorobenzyl |
| $L_3$ | m-xylene |
| $L_4$ | (3-methoxycarbonyl)benzyl |

-continued

| | |
|---|---|
| $L_5$ | 3-nitrobenzyl |
| $L_6$ | α,α,α-trifluoro-m-xylene |

Example 1

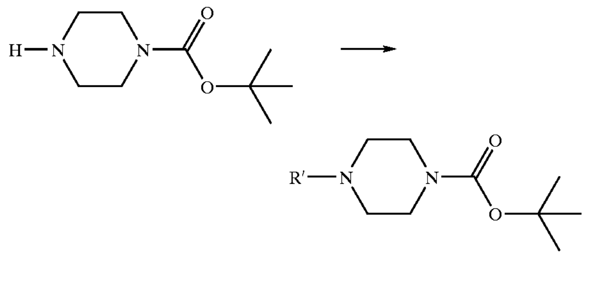

Library 1;
tert-Butyl 4-benzyl-1-piperazinecarboxylate (1), tert-Butyl 4-(3'-methylbenzyl)-1-piperazinecarboxylate (2), tert-Butyl 4-(3'-nitrobenzyl)-1-piperazinecarboxylate (3), tert-Butyl 4-(3'-fluorobenzyl)-1-piperazinecarboxylate (4), tert-Butyl 4-(3'-cyanobenzyl)-1-piperazinecarboxylate (5), tert-Butyl 4-(3'-trifluoromethylbenzyl)-1-piperazinecarboxylate (6) and tert-Butyl 4-(3'-methylcarboxylbenzyl)-1-piperazinecarboxylate (7)

To a solution of tert-butyl 1-piperazinecarboxylate (prepared as per the procedures of Essien, H., *J. Med. Chem.*, 1988, 31, 898) (0.56 g, 3 mmol) in THF (60 mL) was added a mixture of benzyl bromide (360 μL, 3 mmol), 3-methylbenzyl bromide (423 μL, 3 mmol), 3-trifluoromethylbenzyl bromide (460 μL, 3 mmol), 3-fluorobenzyl bromide (372 μL, 3 mmol), methyl 3-(bromomethyl) benzoate (0.72 g, 3 mmol), 3-cyanobenzyl bromide (0.66 g, 3 mmol) and 3-nitrobenzyl bromide (0.6 g, 3 mmol) in the presence of diisopropylethylamine (900 μL, 5.1 mmol). The reaction mixture was stirred at room temperature for 12 hours and then poured into an aqueous mixture of 3-mercapto-1-propanesulfonic acid, sodium salt (7.5 g, 42 mmol) and potassium carbonate (12 g, 84 mmol). The resulting mixture was stirred at room temperature for about 2 hours, concentrated in vacuo and partitioned between ether and water. The aqueous layer was separated and extracted with ether (2×30 mL). The organic layers were combined, dried over $Na_2SO_4$, filtered and concentrated in vacuo to afford a mixture of the title compounds (970 mg)(Library 1).

Mass spectrum: 277 $[M+H]^+$, 291 $[M+H]^+$, 345 $[M+H]^+$, 295 $[M+H]^+$, 335 $[M+H]^+$.

Example 2

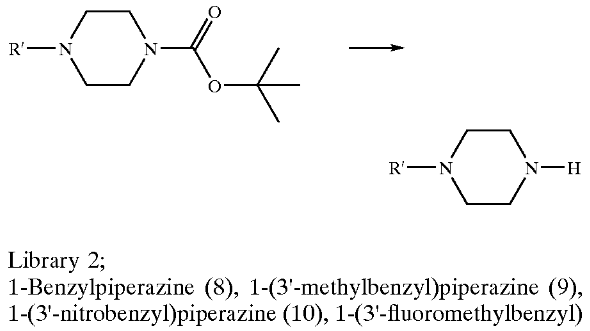

Library 2;
1-Benzylpiperazine (8), 1-(3'-methylbenzyl)piperazine (9), 1-(3'-nitrobenzyl)piperazine (10), 1-(3'-fluoromethylbenzyl) piperazine (11), 1-(3'-cyanobenzyl)piperazine (12), 1-(3'-trifluoromethylbenzyl)piperazine (13) and 1-(3'-methylcarboxylbenzyl)piperazine (14)

To the mixture from Example 1 (3 mmol) in ethanol (20 mL) was added 6 M HCl in ethanol (30 mL, 180 mmol). The reaction mixture was stirred at room temperature for about 12 hours and concentrated in vacuo. The resulting residue was dissolved in water (20 mL), made basic with NaOH and extracted with ethyl acetate (2×30 mL). The organic layers were combined, dried over $Na_2SO_4$, filtered and concentrated in vacuo to afford the title mixture of deprotected compounds (570 mg, 2.72 mmol, 91%).

Mass spectrum: 177 $[M+H]^+$, 191 $[M+H]^+$, 195 $[M+H]^+$, 202 $[M+H]^+$, 222 $[M+H]^+$, 235 $[M+H]^+$ and 245 [M+H].

Example 3

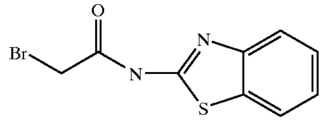

Bromo-N-(2'-benzothiazolyl)acetamide

The title compound was prepared via a modification of the literature procedure of Yuan, J.; Zhang, M., *Beijing Daxue Xuebao, Ziran Kexueban*, 1988, 24, 504–506. To a solution of 2-aminobenzothiazole (7.50 g, 50.0 mmol) in THF (250 mL) was added diisopropylethylamine (9.58 mL, 55.0 mmol). The resulting mixture was cooled to −20° C., and bromoacetyl bromide (4.78 mL, 55.0 mmol) was added slowly. The reaction mixture was warmed to room temperature over 30 minutes and stirred for an additional 30 minutes. The reaction mixture was diluted with water (100 mL), stirred for 30 minutes and further diluted with ethyl acetate (500 mL). The organic layer was separated, washed with water (2×100 mL), washed with brine (100 mL), dried over magnesium sulfate and concentrated in vacuo to afford a purple solid (14.96 g). Recrystallization of the crude product from ethyl acetate provided 8.30 g (61%) of the title compound as a purple solid.

$^1$H-NMR ($Me_2SO-d_6$): δ 12.78 (br, 1H), 8.0-7.3 (m, 4H) and 4.22 (s, 2H). Mass spectrum (FAB+) m/z 271/273 $[M+H]^+$.

Example 4

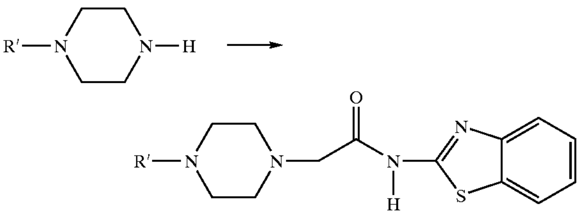

Library 3;
2-[4'-(Benzyl)piperazyl]-N-(2'-benzothiazolyl)acetamide (15), 2-[4'-(3"-methylbenzyl)piperazyl]-N-(2'-benzothiazolyl)acetamide (16), 2-[4'-(3"-nitrobenzyl) piperazyl]-N-(2'-benzothiazolyl)acetamide (17), 2-[4'-(3"-fluoromethylbenzyl) piperazyl]-N-(2'-benzothiazolyl) acetamide (18), 2-[4'-(3"-cyanobenzyl) piperazyl]-N-(2'-benzothiazolyl)acetamide (19), 2-[4'-(3"-trifluoromethylbenzyl) piperazyl]-N-(2'-benzothiazolyl) acetamide (20) and 2-[4'-(3"-methylcarboxylbenzyl) piperazyl]-N-(2'-benzothiazolyl)acetamide (21)

To a mixture of compounds 8–14 (Example 2) (0.45 mmol) in THF (10 mL) was added α-bromo-N-(2'-benzothiazolyl)acetamide (0.186 g, 0.69 mmol) in the presence of diisopropylethylamine (175 μL, 1 mmol). The reaction mixture was stirred at room temperature for 12 hours and then poured into a methanol-water solution containing 3-mercapto-1-propanesulfonic acid, sodium salt (0.125 g, 0.7 mmol) and potassium carbonate (0.2 g, 1.4 mmol). The resulting mixture was stirred at room temperature for 2 hours and concentrated in vacuo and partitioned between water and ether. The aqueous layer was separated and extracted with ether (2×30 mL). The organic layers were combined, dried over $Na_2SO_4$, filtered and concentrated to afford 160 mg (0.41 mmol, 90%) of the title mixture.

Mass Spectrum: ES/MS (367, 381, 385, 392, 412, 435).

Example 5

Bromo-N-cycloheptyl acetamide

To a −20° C. solution of cycloheptylamine (6.37 mL, 50.0 mmol) and diisopropylethylamine (9.58 mL, 55.0 mmol) in methylene chloride (250 mL) was slowly added bromoacetyl bromide (4.78 mL, 55.0 mmol). The reaction mixture was warmed to room temperature over 20 minutes and stirred for an addition 30 minutes. The reaction mixture was diluted with water (100 mL) and stirred for an additional 30 minutes. The organic layer was separated, washed with water (3×100 mL), dried over magnesium sulfate and concentrated in vacuo to afford a beige solid (10.5 g). The crude material was further purified by silica gel flash column chromatography using hexane-ethyl acetate (1:1) as the eluent to give the purified title compound as a white solid (9.77 g, 83%). $^1$H-NMR ($Me_2SO$-$d_6$): δ 8.20 (br d, 1H), 3.77 (s, 2H), 3.67 (m, 1H) and 1.8–1.3 (m, 12H). $^{13}$C-NMR ($CDCl_3$): δ 164.01, 51.04, 34.59, 29.40, 27.80 and 23.87. Mass spectrum (FAB+) m/z 234/236 $[M+H]^+$ and 256/258 $[M+Na]^+$.

Example 6

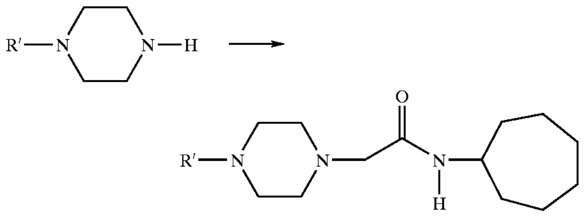

Library 4;

2-[4'-(Benzyl)piperazyl]-N-cycloheptyl acetamide (22), 2-[4'-(3"-methylbenzyl) piperazyl]-N-cycloheptyl acetamide (23), 2-[4'-(3"-nitrobenzyl) piperazyl]-N-cycloheptyl acetamide (24), 2-[4'-(3"-fluoromethylbenzyl) piperazyl]-N-cycloheptyl acetamide (25), 2-[4'-(3"-cyanobenzyl) piperazyl]-N-cycloheptyl acetamide (26), 2-4'-(3"-trifluoromethylbenzyl) piperazyl]-N-cycloheptyl acetamide (27) and 2-[4'-(3"-methylcarboxylbenzyl) piperazyl]-N-cycloheptyl acetamide (28)

To the mixture of compounds 8–4 (Example 2) (0.45 mmol) in THF (10 mL) was added α-bromo-N-cycloheptyl acetamide (0.186 g, 0.69 mmol) in the presence of diisopropylethyl amine (175 μL, 1 mmol). The reaction mixture was stirred at room temperature for 12 hours and then poured into a methanol-water solution containing 3-mercapto-1-propanesulfonic acid, sodium salt (0.125 g, 0.7 mmol) and potassium carbonate (0.2 g, 1.4 mmol). The resulting mixture was stirred at room temperature for about 2 hours and concentrated in vacuo and partitioned between water and ether. The aqueous layer was separated and extracted with ether (2×30 mL). The organic layers were combined, dried over $Na_2SO_4$, filtered and concentrated to afford 150 mg (0.42 mmol, 92%) of the title mixture.

Mass Spectrum: ES/MS (330, 344, 348, 355, 375, 398).

Example 7

Bromo-N-(benzyloxyl)acetamide

To a solution of O-benzylhydroxylamine hydrochloride (1.6 g, 10 mmol) in THF (40 mL) at 0° C., was added bromoacetyl bromide (871 μL, 10 mmol) and diisopropylethylamine (3.5 mL, 20 mmol). The reaction mixture was warmed to room temperature overnight and diluted with ethyl acetate and water. The aqueous layer was separated and extracted with ethyl acetate. The organic layers were combined, dried over $Na_2SO_4$, filtered and concentrated in vacuo. The crude material was purified by silica gel flash column chromatography with ethyl acetate-hexane to give 1.27 g (52%) of the title compound.

TLC ($R_f$=0.5; 40% ethyl acetate-hexane). $^1$H NMR (CDC13): δ 9.21 (br s, 1H, NH), 7.31 (s, 5H, Ar), 4.84 (s, 2H, CH2) and 3.89 (s, 2H, CH2). $^{13}$C NMR (CDC13): δ 163.7, 134.4, 129.5, 129.3, 128.9, 128.6, 78.5 and 40.3.

Example 8

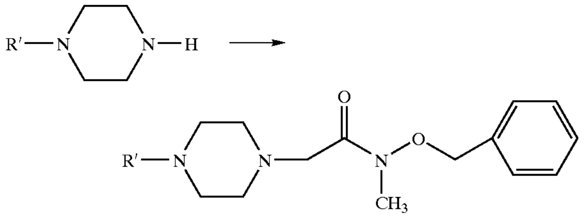

Library 5;

2-[4'-(Benzyl)piperazyl] -N-(O-benzylhydroxyl)acetamide (29), 2-[4'-(3"-methylbenzyl) piperazyl]-N-(O-benzylhydroxyl)acetamide (30), 2-[4'-(3"-nitrobenzyl) piperazyl]-N-(O-benzylhydroxyl)acetamide (31), 2-[4'-(3"-fluoromethyl-benzyl) piperazyl]-N-(O-benzylhydroxyl) acetamide (32), 2-[4'-(3"-cyanobenzyl) piperazyl]-N-(O-benzylhydroxyl)acetamide (33), 2-[4'-(3"-trifluoromethylbenzyl) piperazyl]-N-(O-benzylhydroxyl)acetamide (34) and 2-[4'-(3"-methylcarboxylbenzyl) piperazyl]-N-(O-benzylhydroxyl)acetamide (35)

To the mixture of compounds 8–14 (Example 2) (0.49 mmol) in THF (10 mL) was added bromo-N-(O-benzylhydroxyl)acetamide (0.2 g, 0.8 mmol) in the presence of diisopropylethylamine (520 μL, 3 mmol). The reaction mixture was stirred at room temperature for 12 hours and then poured into a methanol-water solution containing 3-mercapto-1-propanesulfonic acid, sodium salt (0.23 g, 1.3 mmol) and potassium carbonate (0.4 g, 2.6 mmol). The resulting mixture was stirred at room temperature for about 2 hours and concentrated in vacuo and partitioned between water and ether. The aqueous layer was separated and extracted with ether (2×30 mL). The organic layers were combined, dried over $Na_2SO_4$, filtered and concentrated to afford 150 mg (0.42 mmol, 92%) of the title mixture as an oil.

Mass Spectrum: ES/MS (340, 354, 408, 358, 365, 385).

Example 9

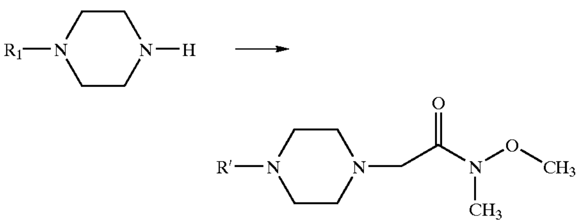

Library 6; 2-[4'-(Benzyl)piperazyl]-N-methoxy-N-methylacetamide (36), 2-[4'-(3"-methylbenzyl) piperazyl]-N-methoxy-N-methylacetamide (37), 2-[4'-(3"-nitrobenzyl) piperazyl]-N-methoxy-N-methylacetamide (38), 2-[4'-(3"-fluoromethylbenzyl) piperazyl]-N-methoxy-N-methylacetamide (39), 2-[4'-(3"-cyanobenzyl) piperazyl]-N-methoxy-N-methylacetamide (40), 2-[4'-(3"-trifluoromethylbenzyl) piperazyl]-N-methoxy-N-methylacetamide (41) and 2-[4'-(3"-methylcarboxylbenzyl) piperazyl ]-N-methoxy-N-methylacetamide (42)

To the mixture of compounds 8–14 (Example 2) (0.49 mmol) in THF (10 mL) was added 2-chloro-N-methoxy-N-methylacetamide (0.12 g, 0.85 mmol) in the presence of diisopropylethylamine (525 $\mu$L, 3 mmol). The reaction mixture was stirred at room temperature for 12 hours and at reflux for 6 hours. The reaction mixture was cooled to room temperature and poured into a methanol-water solution containing 3-mercapto-1-propanesulfonic acid, sodium salt (0.3 g, 1.7 mmol) and potassium carbonate (0.5 g, 3.4 mmol). The resulting mixture was stirred at room temperature for about 2 hours and concentrated in vacuo and partitioned between water and ether. The aqueous layer was separated and extracted with ether (2x30 mL). The organic layers were combined, dried over $Na_2SO_4$, filtered and concentrated to afford 87.3 mg (0.283 mmol, 58%) of the title mixture as an oil.

Mass Spectrum: ES/MS (278, 292, 296, 303, 323, 346).

Example 10

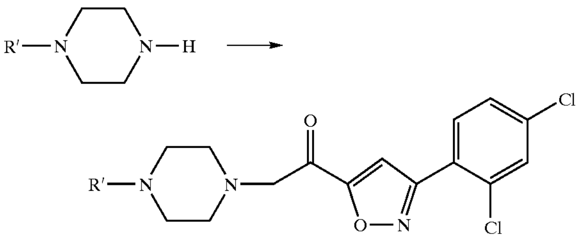

Library 7; 5-[4'-(Benzyl)piperazyl]acetyl-3-(2', 4'-dichlorophenyl) isoxazole (43), 5-[4'-(3"-methylbenzyl)piperazyl]acetyl-3-(2', 4'-dichlorophenyl)isoxazole (44), 2-[4'-(3t"-nitrobenzyl) piperazyl]acetyl-3-(2', 4'-dichlorophenyl)isoxazole (45), 2-[4'-(3"-fluoromethylbenzyl) piperazyl]acetyl-3-(2', 4'-dichlorophenyl)isoxazole (46), 2-[4'-(3"-cyanobenzly) piperazyl]acetyl-3-(2', 4'-dichlorophenyl)isoxazole (47), 2-[4'-(3"-trifluoromethylbenzyl) piperazyl]acetyl-3-(2', 4'-dichlorophenyl)isoxazole (48) and 2-[4'-(3"-methylcarboxylbenzyl]piperazyll acetyl-3-(2', 4'-dichlorophenyl)isoxazole (49)

To the mixture of compounds 8–14 (Example 2) (0.45 mmol) in THF (5 mL) was added 5-(bromoacetyl)-3-(2', 4'-dichlorophenyl)isoxazole (0.015 g, 0.045 mmol) in the presence of diisopropylethylamine (20 $\mu$L, 0.09 mmol). The reaction mixture was stirred at room temperature for 12 hours and then concentrated in vacuo. The resultant residue was diluted with 1 M HCl solution (20 mL) and extracted with ether (2x30 mL). The organic layers were combined, dried over $Na_2SO_4$, filtered and concentrated to afford 18.1 mg (0.035 mmol, 77.8%) of the title mixture as an oil. Mass spectrum: ES/MS (475, 489, 543, 493, 500, 520).

Example 11

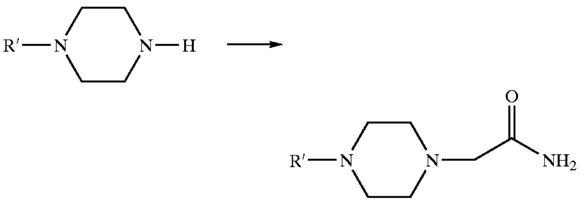

Library 8; (Benzyl)piperazyll acetamide (50), 2-[4'-(3"-methylbenzyl) piperazyl]acetamide (51), 2-[4'-(3"-nitrobenzyl)piperazyl] acetamide (52), 2[4'-(3"-fluoromethylbenzyl)-piperazyl] acetamide (53), 2-[4'-(3"-cyanobenzyl)piperazyl]acetamide (54), 2-[4'-(3"-trifluoromethylbenzyl) piperazyl]acetamide (55) and 2-[4'-(3"-methylcarboxylbenzyl) piperazyl] acetamide (56)

To the mixture of compounds 8–14 (Example 2) (1.29 g, 1.3 mmol) in THF (30 mL) was added α-bromoacetamnide (0.28 g, 2 mmol) in the presence of diisopropylethylamine (460 $\mu$L, 2.6 mmol). The reaction mixture was stirred at room temperature for 12 hours and poured into a methanol-water solution containing 3-mercapto-1-propanesulfonic acid, sodium salt (0.17 g, 1 mmol) and potassium carbonate (0.3 g, 2 mmol). The resulting mixture was stirred at room temperature for 2 hours, concentrated in vacuo and partitioned between water and ether. The aqueous layer was separated and extracted with ether (2x30 mL). The organic layers were combined, dried over $Na_2SO_4$, filtered and concentrated to afford 210 mg (0.8 mmol, 62%) of the title mixture as an oil.

Mass spectrum: ES/MS (234, 248, 252, 259, 279, 302).

Example 12

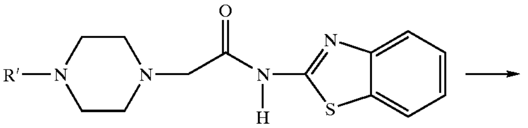

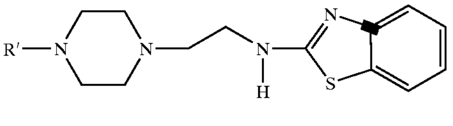

Library 9; 4-[2'-(N-Benzothiazol-2"-yl)amino]ethyl-1-benzyl piperazine (57), 4-[2'-(N-benzothiazol-2"-yl)amino]ethyl-1-(3'-methylbenzyl)piperazine (58), 4-[2'-(N-benzothiazol-2"-yl) amino]ethyl-1-(3'-nitrobenzyl)piperazine (59), 4-[2'-(N-benzo-thiazol-2"-yl)amino]ethyl-1-(3'-fluoromethylbenzyl) piperazine (60), 4-[2'-(N-benzothiazol-2"-yl)amino]ethyl-1-(3'-cyanobenzyl)piperazine (61), 4-[2'-(N-benzothiazol-2"-yl)amino]ethyl-1-(3'-trifluoromethylbenzyl)piperazine (62) and 4-[2'-(N-benzothiazol-2"-yl)amino]ethyl-1-(3'-methylcarboxylbenzyl)piperazine (63)

To the mixture of compounds 15–21 (Example 4) (0.405 mmol) in THF (10 mL) was added a 1 M solution of $BH_3$ in THF (10 mL, 10 mmol). The mixture was stirred at reflux temperature for 24 hours and cooled to room temperature. The reaction mixture was diluted with a 6 M HCl solution (5 mL), stirred at room temperature for 1 hour and concentrated in vacuo. The resultant residue was dissolved in water (20 mL), basified with NaOH and extracted with ethyl acetate (2x20 mL). The organic layers were combined, dried over $Na_2SO_4$, filtered and concentrated to afford 100 mg (0.262 mmol, 64.7%) as an oil.

Mass spectrum: ES/MS (353, 367, 371, 382, 398, 421).

Example 13

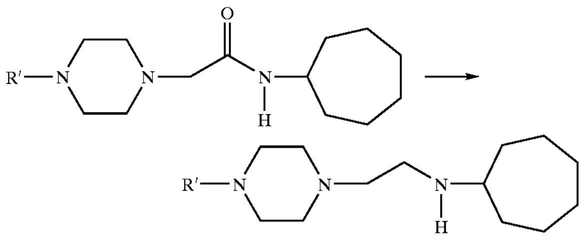

Library 10;

4-[2'-(N-cycloheptyl)amino]ethyl-1-benzyl piperazine (64), 4-[2'-(N-cycloheptyl) amino]ethyl-1-(3'-methylbenzyl) piperazine (65), 4-[2'-(N-cycloheptyl) aminolethyl-1-(3'-nitrobenzyl)piperazine (66), 4-[2'-(N-cycloheptyl)-amino] ethyl-1-(3'-fluoromethylbenzyl)piperazine (67), 4-[2'-(N-cycloheptyl) aminolethyl-1-(3'-cyanobenzyl)piperazine (68), 4-[2'-(N-cycloheptyl)-amino]ethyl-1-(3'-trifluoromethylbenzyl)piperazine (69) and 4-[2'-(N-cycloheptyl)-amino]ethyl-1-(3'-methylcarboxylbenzyl) piperazine (70)

To the mixture of compounds 22–28 (Example 6) (0.41 mmol) in THF (10 mL) was added a 1 M solution of $BH_3$ in THF (10 mL, 10 mmol). The mixture was stirred at reflux temperature for 24 hours and cooled to room temperature. The reaction mixture was diluted with a 6 M HCl solution (5 mL), stirred at room temperature for 1 hour and concentrated in vacuo. The resultant residue was dissolved in water (20 mL), basified with NaOH and extracted with ethyl acetate (2x20 mL). The organic layers were combined, dried over $Na_2SO_4$, filtered and concentrated to afford 114 mg (0.33 mmol, 80.7%) of the title mixture as an oil.

Mass spectrum: ES/MS (316, 330, 334, 342, 361, 384).

Example 14

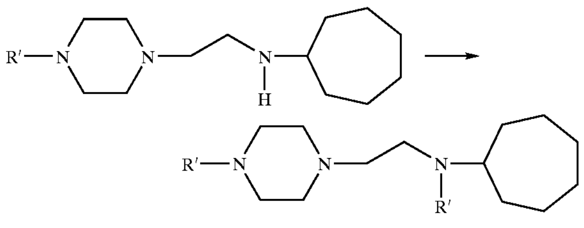

Library 11;

Compounds 106–154

To the mixture of compounds 64–70 (Example 13) (0.023 mmol) in THF (3 mL) was added a mixture of benzyl bromide (3 mL, 0.023 mmol), 3-methylbenzyl bromide (3.2 mL, 0.023 mmol), 3-trifluoromethylbenzyl bromide (3.5 mL, 0.023 mmol), 3-fluorobenzyl bromide (3 mL, 0.023 mmol), 3-cyanobenzyl bromide (5.1 mg, 0.023 mmol) and 3-nitrobenzyl bromide (5 mg, 0.023 mmol) in the presence of diisopropylethylamine (10 mL, 0.046 mmol). The mixture was stirred at room temperature for 12 hours and at reflux for 6 hours. The reaction mixture was cooled to room temperature and poured into a methanol-water solution containing 3-mercapto-1-propanesulfonic acid, sodium salt (0.05 g, 0.28 mmol) and potassium carbonate (0.08 g, 0.58 mmol). The resulting mixture was stirred at room temperature for 2 hours, concentrated in vacuo and partitioned between water and ether. The aqueous layer was separated and extracted with ether (2x20 mL). The organic layers were combined, dried over $Na_2SO_4$, filtered and concentrated to afford 8.4 mg (0.0182 mmol, 79%) of the title library as an oil.

Mass spectrum: ES/MS (406, 420, 424, 431, 434, 438, 442, 445, 451, 465, 469, 474, 488, 492, 499, 519, 542).

Example 15

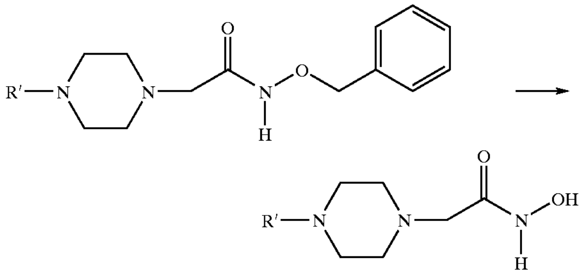

Library 12;

2-[4'-(Benzyl)piperazyl]-N-hydroxyl acetamide (71), 2-[4'-(3"-methylbenzyl) piperazyl]-N-hydroxyl acetamide-(72), 2-[4'-(3"-nitrobenzyl) piperazyl]-N-hydroxyl acetamide (73), 2-[4'-(3"-fluoromethylbenzyl) piperazyl]-N-hydroxyl acetamide (74), 2-[4'-(3"-cyanobenzyl) piperazyl]-N-hydroxyl acetamide (75), 2-[4'-(3"-trifluoromethylbenzyl) piperazyl]-N-hydroxyl acetamide (76) and 2-[4'-(3"-methylcarboxylbenzyl) piperazyl]-N-hydroxyl acetamide (77).

To a mixture compounds 29–35 (0.022 g, 0.062 mmol) in methanol (10 mL) was added 5% palladium on activated carbon (20 mg). The reaction mixture was placed under an atmosphere of hydrogen and stirred at room temperature for 12 hours. The reaction mixture was filtered through a pad of Celite and concentrated to afford 8.2 mg (0.03 mmol, 48.4%) of the title mixture as an oil.

Example 16

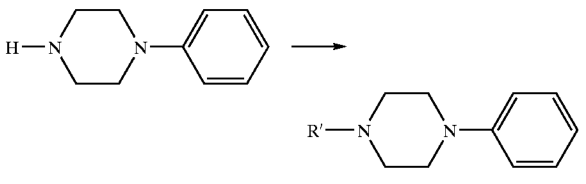

Library 13;

1-Benzyl-4-phenyl piperazine (78), 1-(3'-methylbenzyl)-4-phenyl piperazine (79), 1-(3'-nitrobenzyl)-4-phenyl piperazine (80), 1-(3'-fluorobenzyl)-4-phenyl piperazine (81), 1-(3'-cyanobenzyl)-4-phenylpiperazine (82), 1-(3'-trifluoromethylbenzyl)-4-phenyl piperazine (83) and 1-(3'-methylcarboxylbenzyl)-4-phenyl piperazine (84)

To a solution of N-phenyl piperazine (45 mL, 0.29 mmol) in THF (10 mL) was added a mixture of benzyl bromide (36 mL, 0.3 mmol), 3-methylbenzyl bromide (42.3 mL, 0.3 mmol), 3-trifluoromethylbenzyl bromide (46 mL, 0.3 mmol), 3-fluorobenzyl bromide (37 mL, 0.3 mmol), methyl 3-(bromomethyl)benzoate (0.072 g, 0.3 mmol), 3-cyanobenzyl bromide (0.066 g, 0.3 mmol) and 3-nitrobenzyl bromide (0.06 g, 0.3 mmol) in the presence of diisopropylethylamine (100 mL, 0.5 mmol). The reaction mixture was stirred at room temperature for 12 hours and then poured into a methanol-water solution containing 3-mercapto-1-propanesulfonic acid, sodium salt (0.5 g, 3.15 mmol) and potassium carbonate (1 g, 7 mmol). The mixture was stirred at room temperature for 2 hours and concentrated. The resulting residue was partitioned between ether and water. The aqueous layer was separated and extracted with ether (2×30 mL). The organic layers were combined, washed with brine, dried over $Na_2SO_4$, filtered and concentrated to afford 130 mg of the title library as an oil.

Mass spectrum: ES/MS (253, 267, 271, 278, 298, 311, 321).

Example 17

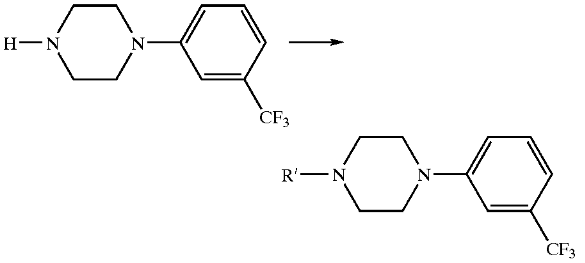

Library 14;

1-Benzyl-4-(3'-trifluoromethylphenyl) piperazine (85), 1-(3'-methylbenzyl)-4-(3'-trifluoromethylphenyl) piperazine (86), 1-(3'-nitrobenzyl)-4-(3'-trifluoromethyl-phenyl) piperazine (87), 1-(3'-fluorobenzyl)-4-(3'-trifluoromethylphenyl) piperazine (88), 1-(3'-cyanobenzyl)-4-(3'-trifluoromethylphenyl)piperazine (89), 1-(3'-trifluoromethylbenzyl)-4-(3'-trifluoromethylphenyl) piperazine (90) and 1-(3'-methylcarboxylbenzyl)-4-(3'-trifluoromethylphenyl)piperazine (91)

To a solution of 1-(3'-trifluoromethylphenyl) piperazine (55 mL, 0.29 mmol) in THF (10 mL) was added mixture of benzyl bromide (36 mL, 0.3 mmol), 3-methylbenzyl bromide (42.3 mL, 0.3 mmol), 3-trifluoromethylbenzyl bromide (46 mL, 0.3 mmol), 3-fluorobenzyl bromide (37 mL, 0.3 mmol), methyl 3-(bromomethyl)-benzoate (0.072 g, 0.3 mmol), 3-cyanobenzyl bromide (0.066 g, 0.3 mmol) and 3-nitrobenzyl bromide (0.06 g, 0.3 mmol) in the presence of diisopropylethylamine (100 mL, 0.5 mmol). The reaction mixture was stirred at room temperature for 12 hours and then poured into a methanol-water solution containing 3-mercapto-1-propanesulfonic acid, sodium salt (0.5 g, 3.15 mmol) and potassium carbonate (1 g, 7 mmol). The mixture was stirred at room temperature for 2 hours and concentrated. The resulting residue was partitioned between ether and water. The aqueous layer was separated and extracted with ether (2×30 mL). The organic layers were combined, washed with brine, dried over $Na_2SO_4$, filtered and concentrated to afford the title library as an oil (89.1 mg, 0.252 mmol, 87.1%).

Mass spectrum: ES/MS (321, 335, 339, 346, 366, 379, 389).

Example 18

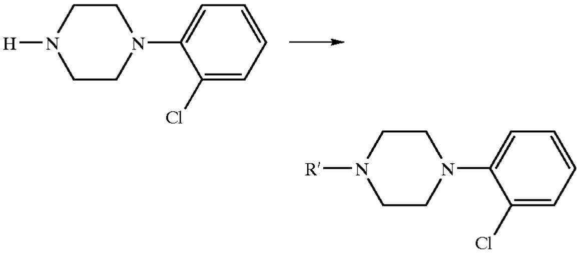

Library 15;

1-Benzyl-4-(2'-chlorophenyl) piperazine (92), 1-(3'-methylbenzyl)-4-(2'-chlorophenyl) piperazine (93), 1-(3'-nitrobenzyl)-4-(2'-chlorophenyl) piperazine (94), 1-(3'-fluorobenzyl)-4-(2'-chlorophenyl) piperazine (95), 1-(3'-cyanobenzyl)-4-(2'-chlorophenyl) piperazine (96), 1-(3'-trifluoromethylbenzyl)-4-(2'-chlorophenyl) piperazine (97) and 1-(3'-methylcarboxylbenzyl)-4-(2'-chlorophenyl) piperazine (98)

To a solution of 1-(2-chlorophenyl)piperazine monohydrochloride (67 mg, 0.29 mmol) in THF (10 mL) was added a mixture of benzyl bromide (36 mL, 0.3 mmol), 3-methylbenzyl bromide (42.3 mL, 0.3 mmol), 3-trifluoromethylbenzyl bromide (46 mL, 0.3 mmol), 3-fluorobenzyl bromide (37 mL, 0.3 mmol), methyl 3-(bromomethyl)benzoate (0.072 g, 0.3 mmol), 3-cyanobenzyl bromide (0.066 g, 0.3 mmol) and 3-nitrobenzyl bromide (0.06 g, 0.3 mmol) in the presence of diisopropylethylamine (200 mL, 1 mmol). The reaction mixture was stirred at room temperature for 12 hours and then poured into a methanol-water solution containing 3-mercapto-1-propanesulfonic acid, sodium salt (0.5 g, 3.15 mmol) and potassium carbonate (1 g, 7 mmol). The mixture was stirred at room temperature for 2 hours and concentrated. The resulting residue was partitioned between ether and water. The aqueous layer was separated and extracted with ether (2×30 mL). The organic layers were combined, washed with brine, dried over $Na_2SO_4$, filtered and concentrated to afford 79 mg (0.247 mmol, 85.2%) of the title library as an oil.

Mass spectrum: ES/MS 287, 301, 305, 312, 332, 345, 355.

Example 19

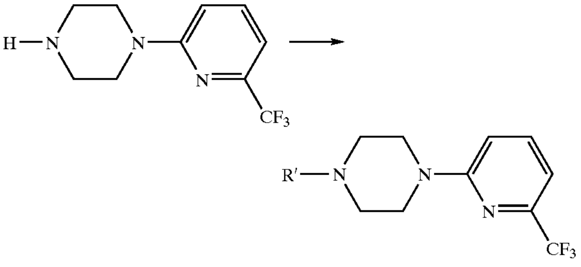

Library 16;

1-Benzyl-4-[6'-(trifluoromethyl)pyrid-2'-yl] piperazine (99), 1-(3'-methylbenzyl)-4-16'-(trifluoromethyl)pyrid-2'-yl] piperazine (100), 1-(3'-nitrobenzyl)-4-[6'-(trifluoro-methyl) pyrid-2'-yl] piperazine (101), 1-(3'-fluorobenzyl)-4-[6'-(trifluoro-methyl)pyrid-2'-ylπ piperazine (102), 1-(3'-cyanobenzyl)-4-[6'-(trifluoromethyl) pyrid-2'-yl] piperazine (103), 1-(3'-trifluoromethylbenzyl)-4-[6'-(trifluoromethyl) pyrid-2'-yl] piperazine (104) and 1-(3'- methylcarboxylbenzyl)-4-[6'-(trifluoromethyl)pyrid-2'-yl] piperazine (105)

To a solution of 1-[6-(trifluoromethyl)pyrid-2-yl] piperazine (0.069 g, 0.3 mmol) in THF (10 mL) was added a mixture of benzyl bromide (36 mL, 0.3 mmol), 3-methylbenzyl bromide (42.3 mL, 0.3 mmol), 3-trifluoromethylbenzyl bromide (46 mL, 0.3 mmol), 3-fluorobenzyl bromide (37 mL, 0.3 mmol), methyl 3-(bromomethyl)benzoate (0.072 g, 0.3 mmol), 3-cyanobenzyl bromide (0.066 g, 0.3 mmol) and 3-nitrobenzyl bromide (0.06 g, 0.3 mmol) in the presence of diisopropylethylamine (100 mL, 0.5 mmol). The reaction mixture was stirred at room temperature for 12 hours and then poured into a methanol-water solution containing 3-mercapto-1-propanesulfonic acid, sodium salt (0.5 g, 3.15 mmol) and potassium carbonate (1 g, 7 mmol). The mixture was stirred at room temperature for 2 hours and concentrated. The resulting residue was partitioned between ether and water. The aqueous layer was separated and extracted with ether (2×30 mL). The organic layers were combined, washed ith brine, dried over $Na_2SO_4$, filtered and concentrated to afford 98.3 mg (0.28 mmol, 93.3%) of the title library as an oil.

Mass spectrum: ES/MS (322, 336, 340, 347, 367, 380, 390).

Example 20

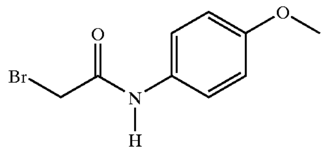

Bromo-N-(4-methoxyphenyl) acetamide

The title compound was prepared via a modification of the literature procedure (Vloon, W. J.; Kruk, C.; Pandit, U. K.; Hofs, H. P.; McVie, J. G. *J. Med. Chem.* 1987, 30, 20–4.). To a solution of 4-methoxyaniline (4.93 g, 40.0 mmol) in methylene chloride (200 mL) was added diisopropylethylamine (7.66 mL, 44.0 mmol). The resulting mixture was cooled to −20° C., and bromoacetyl bromide (3.82 mL, 44.0 mmol) was added slowly. The reaction mixture was warmed to room temperature over 20 minutes and stirred additional 30 minutes. The reaction mixture was diluted with water (100 mL), stirred for 30 minutes and the organic layer was separated. The organic layer was washed with water (2×100 mL), brine (100 mL), dried over magnesium sulfate and concentrated in vacuo to afford a beige solid (9.68 g) which was recrystallized from ethyl acetate to provide bromo-N-(4'-methoxyphenyl) acetamide as a white crystal (6.31 g, 65%).

Example 21

Library 17

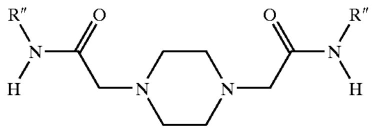

where each R" is independently of the structure:

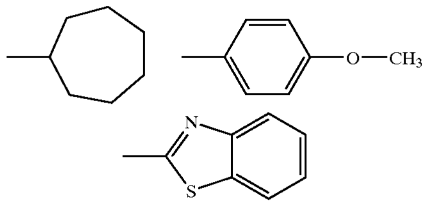

A solution of piperazine (0.056 g, 0.65 mmol) in THF (20 mL) was treated with a mixture of bromo N-cycloheptyl acetamide (0.094 g, 0.4 mmol), bromo N-(benzothiazol-2'-yl) acetamide (0.094 g, 0.4 mmol) and bromo N-(4'-methoxyphenyl) acetamide (0.11 g, 0.4 mmol) in the presence of diisopropylethylamine (320 μL, 1.8 mmol). The mixture was stirred at room temperature for 12 hours. The reaction mixture was then poured into a methanol-water solution of 3-mercapto-1-propanesulfonic acid, sodium salt (0.43 g, 2.4 mmol) and potassium carbonate (0.7 g, 4.8 mmol). The mixture was stirred at room temperature for 2 hours and concentrated in vacuo. The resultant residue was partitioned between ether/$H_2O$ and extracted with ether (2×30 mL). The organic layer was dried ($Na_2SO_4$), filtered and concentrated in vacuo to give the title group of compounds 220 mg (0.52 mmol, 80%) as an oily residue. The title group of compounds was further identified by ES/MS (413, 467, 393, 403, 430, 440).

Library 18

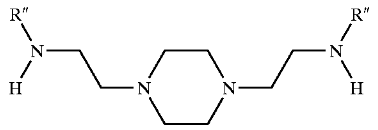

where each R" is independently of the structure:

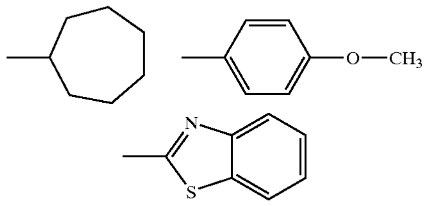

A mixture of solution of compounds in Example 4 (160 mg, 0.52 mmol) in THF (30 mL) was treated with 1 M $BH_3$/THF (2.08 mmol, 2 mL) under an atmosphere of argon. The mixture was stirred at reflux temperature for 12 hours. The reaction mixture was cooled to room temperature and 6 M HCl solution (2 mL) was added. The mixture was stirred at room temperature for about 30 minutes and concentrated in vacuo. The resultant residue was dissolved in $H_2O$ (20 mL), basified with NaOH and extracted with ether (2×30 mL). The organic layer was dried ($Na_2SO_4$), filtered and concentrated in vacuo to give the title group of compounds 117 mg (0.29 mmol, 77%) as an oily residue. The title group of compounds was further identified by ES/MS (365, 375, 385, 402, 412, 439).

Example 23

Library

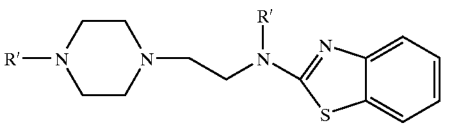

The combinatorial library of Example 12 is treated as per the procedures of Example 14 to give the title combinatorial library.

Example 24

Library 20

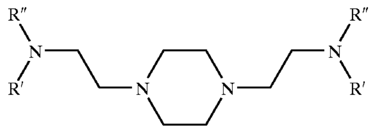

where each R' is as described above and each R" is independently of the structure:

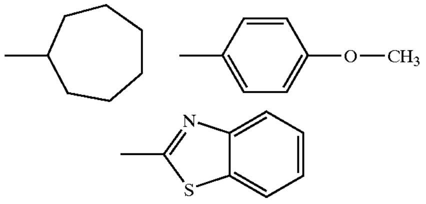

The combinatorial library of Example 22 is treated as per the procedures of Example 14 to give the title combinatorial library Example 25

1-O-Phthalimido-3-bromo-1-propanol

A mixture of N-hydroxyphthalimide (16.3 g, 100 mmol) and 1,3-dibromopropane (20.19 g, 100 mmol) in dry DMF (150 mL) and triethyl amine (15.33 mL, 110 mmol) is stirred at 20 to 75° C. for 1 to 10 hours. After filtration, the mixture is evaporated to dryness in vacuo. The residue is purified by silica gel flash column chromatography to give the title compound.

Example 26

N,N-(bis-orthonitrobenzenesulfonyl)diaminoethane

A solution of 2-nitrobenzenesulfonyl chloride (Aldrich, 10.64 g, 47.0 mmol, 2.3 eq) in dichloromethane (60 mL) is added dropwise to a stirred solution of ethylenediamine (1.33 mL, 20.0 mmol) and triethylamine (16 mL) in dichloromethane (80 mL) at 0° C. The resulting reaction mixture is allowed to warm to room temperature and further stirred for 2 hours. The mixture is diluted with chloroform and washed with water and brine. The organic phase is dried ($Na_2SO_4$) and the solvent is evaporated under the reduced pressure. The residue is purified by flash chromatography on a silica gel column (20 cm×6 cm). Elution with hexanes:ethyl acetate (2:1 and 1:1, v/v) will give the title compound.

Example 27

1-O-phthalimido-3-N-(N-orthonitrobenzenesulfonyl-aminoethyl-2-yl)-N-orthonitrobenzenesulfonyl)-3-amino-1-propanol A mixture of N,N-(bis-nitrobenzenesulfonyl) diaminoethane (400 mmol) and 1-O-phthalimido-3-bromo-1-propanol (400 mmol) is stirred at 20 to 75° C. for 1 to 25 hours. After filtration, the mixture is evaporated to dryness under reduced pressure. The residue is distributed between water and ethyl acetate. The organic layer is separated, dried ($MgSO_4$), and concentrated in vacuo to dryness. The residue is purified by silica gel flash column chromatography to give the title compound.

Example 28

1-O-amino-3-N-(N-orthonitrobenzenesulfonyl-aminoethyl-2-yl)-N-orthonitrobenzenesulfonyl)-3-amino-1-propanol 1-O-phthalimido-3-N-(N-orthonitrobenzenesulfonyl-aminoethyl-2-yl)-N-orthonitrobenzenesulfonyl)-3-amino-1-propanol (20.97 mmol) is suspended in Ethanol (absolute, 300 mL). To this solution is added hydrazine (5 eq. 105 mmol, 3.3 mL) in one portion. The reaction mixture is stirred for 6 hours at which time the resulting white precipitate is filtered off. The filtrate is concentrated under vacuo. To the residue is added ethyl ether (150 ml), and the resulting solid is filtered, and the filtrate is concentrated. The resulting solid is purified by silica gel flash column chromatography using dichloromethane: MeOH followed by dichloromethane:$NH_4OH$:MeOH as the eluents. The desired fractions are combined, concentrated, and dried to give the title compound.

Example 29

1O-(N-t-Boc-amino)-3-N-(N-orthonitrobenzenesulfonyl-aminoethyl-2-yl)-N-orthonitrobenzenesulfonyl)-3-amino-1-propanol 1-O-amino-3-N-(N-orthonitrobenzenesulfonyl-aminoethyl-2-yl)-N-orthonitrobenzenesulfonyl)-3-amino-1-propanol(70 mmol) is dissolved in $CH_3CN$ (250 mL) and triethyl amine (11 mL, 77 mmol) and di-t-butyl dicarbonate (15.2 mL, 66.5 mmol) is added. The reaction mixture is stirred at room temperature for 12 hours under an atmosphere of argon. Saturated $NaHCO_3$ (200 mL, aq) was added and stirring is continued for 15 minutes. The mixture is poured into a separatory funnel and extracted several times with ether. The combined ether extracts are dried over $Na_2SO_4$. The dried ether layer is filtered and concentrated in vacuo to give the title compound.

Example 30

2-N-t-Boc-7,10-bis-N-orthonitrobenzenesulfonyl-2,7,10-triaza-3-oxaundecanel11](2,6) pyridinophane A mixture of 1-O-(N-t-Boc-amino)-3-N-(N-orthonitrobenzenesulfonyl-aminoethyl-2-yl)-N-orthonitrobenzenesulfonyl)-3-amino-1-propanol (5.0 mmol, 1 eq), 2,6-bis(bromomethyl)pyridine (Aldrich, 1.33 g, 5.0 mmol) and cesium carbonate (6.52 g, 29 mmol, 4 eq) in anhydrous DMF (160 mL) is stirred at room temperature for 24 hours. The solvent is evaporated under reduced pressure and the residue is dissolved in a mixture of water and chloroform. The layers are separated and the aqueous phase is extracted with chloroform. The organic extract is washed with brine, dried ($Na_2SO_4$) and concentrated. The residue is purified by flash chromatography on a silica gel column. Elution with hexanes:ethyl acetate will give the title compound.

Example 31

2-N-t-Boc-2,7,10-triaza-3-oxaundecane[11](2,6) pyridinophane

Thiophenol (Aldrich, 500 μL, 0.53 g, 4.8 mmol, 2.4 eq) is added to a stirred mixture 2-N-t-Boc-7,10-bis-N-orthonitrobenzenesulfonyl-2,7,10-triaza-3-oxaundecane-[11](2,6) pyridinophane (2.0 mmol) and potassium carbonate (2.21 g, 16 mmol, 8 eq.) in DMF (30 mL). The resulting mixture is stirred at room temperature for 2 hours. The reaction mixture is concentrated under reduced pressure and the residue is dissolved in water. The solution is made basic (e.g. pH 13–14) with aqueous sodium hydroxide and extracted with chloroform. The organic extract is washed with brine, dried ($Na_2SO_4$) and the solvent is evaporated. The residue is purified by flash chromatography on a silica gel column. Elution with methanol and methanol:30% aqueous ammonium hydroxide will give the title compound.

Example 32

Library 21, 2-N-t-Boc-7,10-bis-($L_1$–$L_6$)-2,7,10-triaza-3-oxaundecane[11](2,6) pyridinophane A solution of benzyl bromide (123 μL, 171 mg, 1.0 mmol), 3-fluorobenzylbromide (124 μL, 189 mg, 1.0 mmol), α-bromo-m-xylene (141 μL, 185 mg, 1.0 mmol), methyl-3-bromomethylbenzoate (229 mg, 1.0 mmol), 3-nitrobenzyl bromide (216 mg, 1.0 mmol) and α'-bromo-α,α,α-trifluoro-m-xylene (155 μL, 239 mg, 1.0 mmol) in acetonitrile (30 mL) is added to a stirred mixture of 2-N-t-Boc-2,7,10-triaza-3-oxaundecane[11](2,6) pyridinophane (1.65 mmol) and potassium carbonate (3.5 g, 25.0 mmol) in acetonitrile (60 mL). The resulting reaction mixture is stirred at room temperature overnight. The solvent is evaporated and the resulting residue is dissolved in water and chloroform. The layers are separated and the aqueous layer is extracted with chloroform. The chloroform extract is washed with brine, dried ($Na_2SO_4$), and filtered. The solvent is evaporated and the resulting residue is purified by flash chromatography on a silica gel column. Elution with hexanes:ethyl acetate and then ethyl acetate will give the title library.

Example 33

Library 22, 2-(N-t-Boc-aminomethylene)-6-{N1-[($L_1$–$L_6$) methylene-1-yl]-N2-[1-propanol-3-yl]-N2-(($L_1$–$L_6$)-1,2-diaminoethane}pyridine Library 21 (0.025 molar) is dissolved in dry MeOH, cooled to 0° C., and $NaBH_3CN$ (50 eq.) is added slowly. The reaction mixture is stirred at 0° C. for 1.5 hours and then at room temperature for 16 hours. The reaction mixture is concentrated in vacuo and the residue left behind is partitioned between EtOAc and $H_2O$ (100 mL, 1:1, v/v). The $H_2O$ layer is separated and extracted with EtOAc (3×50 mL). The EtOAc extracts are dried ($MgSO_4$), filtered and the filtrate is concentrated in vacuo. The resulting residue is purified by silica gel flash column chromatography using $MeOH/CH_2Cl_2$ as the eluent. The appropriate fractions are pooled and concentrated in vacuo to give the title Library.

Example 34

Library 23,2-[N-(t-Boc)N-($L_1$–$L_6$)aminomethylenel-6-{N1-[($L_1$–$L_6$)methylene-1-yl]-N2-1-propanol-3-yl]-N2-(($L_1$–$L_6$)-1,2-diaminoethane}pyridine Library 22 is treated as per the procedures of Example 32 with a solution of benzyl bromide (123 μL, 171 mg, 1.0 mmol), 3-fluorobenzylbromide (124 μL, 189 mg, 1.0 mmol), α-bromo-m-xylene (141 μL, 185 mg, 1.0 mmol), methyl-3-bromo-methylbenzoate (229 mg, 1.0 mmol), 3-nitrobenzyl bromide (216 mg, 1.0 mmol) and α'-bromo-(α,α,α-trifluoro-m-xylene (155 μL, 239 mg, 1.0 mmol) in acetonitrile (30 mL) to give, after purification, the title library.

Example 35

Library 24, 2-[N-($L_1$–$L_6$)aminomethylene]-6- {N1-[($L_1$–$L_6$) methylene-1-yl]-N2-[1-propanol-3-yl]-N2-(($L_1$–$L_6$)-1,2-diaminoethane}pyridine Trifluoroacetic acid (TFA) (8 mL) is added to a flask containing Library 23 (1.04 mmol) at 0° C. The resulting solution is stirred at room temperature for 3 hours. The TFA is evaporated under reduced pressure and the residue is dissolved in chloroform (200 mL). The resulting solution is washed 3 times with saturated solution of aqueous potassium carbonate, dried ($Na_2SO_4$), and filtered. The solvent is evaporated and the residue is purified by flash column chromatography on a silica gel column. Elution with methanol and then methanol:30% aqueous ammonium hydroxide (100:1, v/v) will give the title library.

Example 36

Library 25, 2-[N-di($L_1$–$L_6$)aminomethylene]-6-{N1-[($L_1$–$L_6$)methylene-1-yl]-N2-[1-propanol-3-yl]-N2-(($L_1$–$L_6$)-1,2-diaminoethane}pyridine Library 24 is treated as per the procedures of Example 32 with a solution of benzyl bromide (123 μL, 171 mg, 1.0 mmol), 3-fluorobenzylbromide (124 μL, 189 mg, 1.0 mmol), α-bromo-m-xylene (141 μL, 185 mg, 1.0 mmol), methyl-3-bromo-methylbenzoate (229 mg, 1.0 mmol), 3-nitrobenzyl bromide (216 mg, 1.0 mmol) and α'-bromo-α,α,α-trifluoro-m-xylene (155 μL, 239 mg, 1.0 mmol) in acetonitrile (30 mL) to give, after purification, the title library.

Example 37

Diethyl-4-bromo-2,6-pyridinedicarboxylate

A mixture of chelidamic acid (2.29 g, 11.38 mmol) and phosphorus pentabromide (14.7 g, 34.14 mmol) was stirred for 3 hours at 90° C. The reaction mixture was cooled to room temperature and $CHCl_3$ (350 mL) was added. The resulting mixture was filtered and to the filtrate was added absolute ethanol (350 mL). The mixture was stirred for 2 hours and then the volume of the reaction mixture was reduced to approximately 35 mL in vacuo. The title compound was purified first by crystallization upon sitting overnight followed by purification by silica gel flash column chromatography to give a yield of 72% of the title compound.

(m. p. 95–96° C.). $^1H$ NMR ($CDCl_3$) δ 1.49 (t, 6H, 2×$CH_3$), 4.44 (q, 4H, 2×$CH_2$), 8.39 (s, 2H, 2×Ar). $^{13}C$ NMR ($CDCL_3$) δ 14.19 ($CH_3$), 62.68 ($CH_2$), 131.02 (Ar), 134.87 (quaternary-Ar), 149.54 (quaternary-Ar), 163.51 (CO).

Example 38

Diethyl-4-(3-azidopropoxy)-2,6-pyridinedicarboxylate

3-Azido-1-propanol (0.266 mL, 3.64 mmol) was dissolved in DMF (5 mL) and cooled to 0° C. NaH (146 mg, 3.64 mmol) was added and the mixture was stirred for 15 minutes. Diethyl-4-bromo-2,6-pyridinedicarboxylate dissolved in DMF (5 mL) was added to the reaction mixture dropwise. The reaction was complete as indicated by TLC in 1 hour. The reaction mixture was partitioned between $CH_2Cl_2$ and water. The water was separated and extracted with $CH_2Cl_2$. The $CH_2Cl_2$ layers were combined, dried ($MgSO_4$) and concentrated to an oil. The oil was purified by silica gel flash column chromatography to give a yield of 40% of the title compound.

$^1H$ NMR ($CDCl_3$) δ 1.44 (t, 6H, 2×$CH_2$), 2.11 (m, 2H, $CH_2$), 3.54 (t, 2H, $CH_2$), 4.23 (t, 2H, $CH_2$), 4.45 (q, 4H, 2×$CH_2$), 7.78 (2, 2H, 2×Ar).

Example 39

4-(3-Azidopropoxy)-2,6-dihydroxymethylpyridine

To a stirred solution of diethyl-4-(3-azidopropoxy)-2,6-pyridinedicarboxylate (4.2 mmol) in dichloromethane (10 mL) and absolute ethanol (15 mL), was added in portions, $NaBH_4$ (4.2 mmol) at 25° C. Powdered $CaCl_2$ (4.2 mmol) was added cautiously in small portions and the evolution of hydrogen was allowed to cease before each further addition. The reaction mixture was stirred for 2 hours. Water (100 mL) was added and the reaction mixture was extracted several times with ethyl acetate. The ethyl acetate layers were combined, dried ($MgSO_4$) and concentrated in vacuo. The resultant residue was purified by silica gel flash column chromatography to give the title compound.

$^1H$ NMR (DMSO) δ 2.00 (m, 2H, $CH_2$), 3.52 (t, 2H, $CH_2$), 4.13 (t, 2H, $CH_2$), 4.45 (d, 4H, 2×$CH_2$), 5.36 (t, 2H, 2×OH), 6.87 (s, 2H, 2×AR).

Example 40

4-(3-Azidopropoxy)-2,6-bis-dibromomethylpyridine 4-(3-Azidopropoxy)-2,6-dihydroxymethylpyridine is treated with an excess of phosphorous tribromide in a traditional solvent to give after neutralization and purification the title compound.

Example 41

2-N-t-Boc-7,10-bis-N,N-orthonitrobenzenesulfonyl-2,7,10-triaza-3-oxaundecanel [11](2,6)-4-azidopropoxy pyridinophane 4-(3-Azidopropoxy)-2,6-dihydroxymethylpyridine (177 mmol), and 1-O-(N-t-Boc) amino-3-N-(N-orthonitrobenzenesulfonyl-aminoethyl-2-yl)-N-orthonitrobenzenesulfonyl)-3-amino-1-propanol (42.13 mmol) is stirred in THF (80 mL) at room temperature under an atmosphere of argon. Sodium carbonate (21 g, 198 mmol) is added and the reaction mixture is equilibrated to room temperature with stirring for 12 hours. $NaH_2PO_4$ (100 mL, 0.5 M, aq) is added and the aqueous layer is separated and extracted with toluene. The aqueous layer is made basic with NaOH and extracted with ether. The combined ether extracts are dried over $Na_2SO_4$. The dried ether layer is filtered and evaporated to a residue. The residue is purified by silica gel flash column chromatography using $MeOH/CH_2C_2$ as the eluent. The target fractions are pooled together and evaporated to dryness to give the title compound.

Example 42

2-N-t-Boc-2,7,10-triaza-3-oxaundecane[11](2,6)-4-azidopropoxy pyridinophane

2-N-t-Boc-7,10-bis-N,N-orthonitrobenzenesulfonyl-2,7,10-triaza-3-oxaundecane[11](2,6)-4-azidopropoxy pyridinophane is treated as per the procedure of Example 31 to give the title compound.

Example 43

Library 26, 2-N-t-Boc-7,10-bis-N,N-($L_1$–$L_6$)-2,7,10-triaza-3-oxaundecane[11](2,6)-4-azidopropoxy pyridinophane 2-N-t-Boc-2,7,10-triaza-3-oxaundecane[11](2,6)-4-azidopropoxy pyridinophane is treated as per the procedures of Example 32 to give the title library.

Example 44

Library 27, 2-(N-t-Boc-aminomethylene)-6-{N1-[($L_1$–$L_6$) methylene-1-yl]-N2-[1-propanol-3-yl]-N2-(($L_1$–$L_6$)-1,2-diaminoethane}4-aminopropoxypyridine Library 26 is treated as per the procedures of Example 33 to give the title library.

Example 45

Library 28, 2-{N-[(t-Boc-aminomethylene)($L_1$–$L_6$)}-6-{N1-[($L_1$–$L_6$)methylene-1-yl]-N2-1-propanol-3-yl]-N2-(($L_1$–$L_6$)-1,2-diaminoethane}4-[N-di($L_1$–$L_6$)]-aminopropoxy-opyridine Library 27 is treated as per the procedures of Example 32 to give the title library.

Example 46

Library 29; 2-{N-$L_1$–$L_6$-aminomethylene}-6-{N1-[($L_1$–$L_6$) methylene-1-yl]-N2-[1-25 propanol-3-yl]-N2-($L_1$–$L_6$)-1,2-diaminoethane}4-N-di($L_1$–$_6$)1-aminopropoxypyridine Library 28 is treated as per the procedures of Example 35 to give the title library.

Example 47

Library 30, 2- {N-di-$L_1$–$L_6$-aminomethylene)}-6-{N1-[($L_1$–$L_6$)methylene-1-yl]-N2-[1-propanol-3-yl]-N2-(($L_1$–$L_6$)-1,2-diaminoethane}-4-[N-di($L_1$–$L_6$)]-aminopropoxy-pyridine Library 29 is treated as per the procedures of Example 32 to give the title library.

Example 48

[4-O-(t-butyldiphenylsilyl)]-butyraldehyde-4-ol

A mixture of 4-penten-1-ol (10 mmol), t-butyldiphenylsilylchloride (12 mmol), imidazole (25 mmol) and dry DMF (50 ml) is stirred at room temperature for 16 hours under an atmosphere of argon. The reaction mixture is poured into ice-water (200 ml) and the solution extracted with $CH_2Cl_2$ (2×200 ml). The organic layer is washed with water (2×200 ml) and dried ($MgSO_4$). The $CH_2Cl_2$ layer is concentrated to furnish a residue, which on purification by silica gel chromatography gives silylated 4-penten-1-ol. The silylated compound is oxidized with $OSO_4$ (1 mmol) and N-methylmorpholine oxide (20 mmol) in diethyl ether (40 ml) and water (20 ml) at room temperature for 18 hours. $NaIO_4$ (30 mmol) solution in water (2 ml) is added to the above solution and stirring is continued for 12 hours. The aqueous layer is extracted with diethyl ether (2×200 ml) and the ether layers are combined. The resulting organic layer is evaporated to dryness to give the crude title compound.

Example 49

4-[O-(t-butyidiphenylsilyl)]-1-(N,N'-diphenylimidazolidine)butan-4-ol

[4-O-(t-butyldiphenylsilyl)]-butyraldehyde-4-ol is converted to the N,N'-diphenylimidazolidine derivative utilizing the procedure of Giannis, et. al., Tetrahedron 1988, 44, 7177, to furnish the title compound.

Example 50

4-(O-phthalimido)-1-(N,N'-diphenylimidazolidine)butan-4-ol

4-[O-(t-butyldiphenylsilyl)]-1-(N,N'-diphenylimidazolidine)butan-4-ol is treated with $Bu_4NF$/THF to remove the silyl protecting group. The hydroxyl group of the latter compound is treated with N-hydroxyphthalimide in a manner described by Debart, et. al., *Tet. Lett*. 1992, 33, 2645, to give the title compound.

Example 51

Functionalization of the solid support

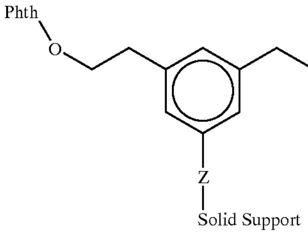

The solid support is functionalized as illustrated above from trisubstituted benzene following a double Mitsunobu reaction described in *Tet. Lett*. 1992, 33, 2645 and loading of the product via succinyl linker (Z) onto a CPG support (see, e.g., R. T. Pon in Protocols For Oligonucleotides And Analogs, Chapter 24, Agrawal, S., ed., Humana Press, Totowa, N.J., 1993.).

Example 52

Formation of the Oxime

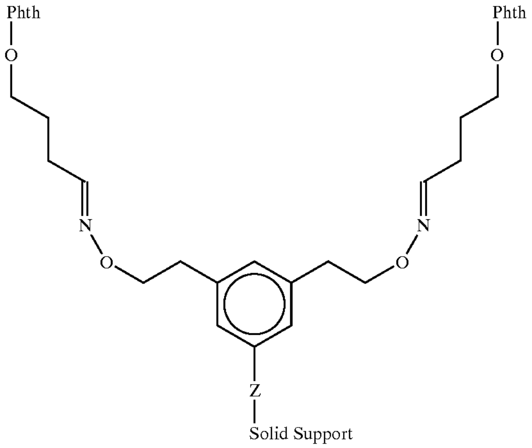

The CPG bound material from Example 51 is packed into a 1 μM column and attached to an ABI DNA synthesizer 380 B model. Bis-phthalimido groups are deblocked with 3% N-methyl hydrazine/$CH_2Cl_2$ solution to liberate desired bis-O-amino moieties. The deblocked CPG bound material is then treated with 4-(O-phthalimido)-1-(N,N'-diphenylimidazolidine)butan-4-ol is employed with 5% AcOH/$CH_2Cl_2$ to give the bis-oxime. The bis-oxime is cleaved from the solid support using standard methods and techniques known to the art skilled.

Example 53

Reductive alkylation with $L_1$–$L_6$

The CPG bound material formed in Example 52 is removed from the synthesizer and treated with ACOH/$NaCNBH_3$ to reduce the oxime to the hydroxyl amine. The two secondary amine sites are subsequently treated as per the procedure of Example 32 with a mixture of reactant compounds to give a composition of compounds.

Example 54

Diethyl-4-bromo-2,6-pyridinedicarboxylate

To chelidamic acid (2.29 g, 11.38 mmol) was added phosphorus pentabromide (14.7 g, 34.14 mmol), and the mixture was stirred. The reaction mixture was heated to 90° C. for 3 hours. The reaction mixture was cooled and $CHCl_3$ (350 mL) was added and the mixture was filtered. To the filtrate was added absolute ethanol (350 mL), and the mixture was stirred for 2 hours. The volume of the reaction mixture was reduced to approximately 35 mL. The title compound was purified by crystallization upon sitting overnight to give, after a second crop of crystals and purification by silica gel flash column chromatography a yield of 72% (m. p. 95–96° C.). $^1H$ NMR ($CDCl_3$) δ 1.49 (t, 6H, 2×$CH_3$), 4.44 (q, 4H, 2×$CH_2$), 8.39 (s, 2H, 2×Ar). $^{13}C$ NMR ($CDCL_3$) δ 14.19 ($CH_3$), 62.68 ($CH_2$), 131.02 (Ar), 134.87 (quaternary-Ar), 149.54 (quaternary-Ar), 163.51 (CO).

Example 55

Diethyl-4-(3-azidopropoxy)-2,6-pyridinedicarboxylate

METHOD A

3-Azido-1-propanol (0.266 mL, 3.64 mmol) was dissolved in DMF (5 mL) and cooled to 0° C. NaH (146 mg, 3.64 mmol) was added and the mixture was stirred for 15 minutes. Diethyl-4-bromo-2,6-pyridinedicarboxylate was dissolved in DMF (5 mL) an added to the reaction mixture dropwise. The reaction was complete as indicated by TLC in 1 hour. The reaction mixture was partitioned between $CH_2Cl_2$ and water. The water was separated and extracted with $CH_2Cl_2$. The $CH_2Cl_2$ layers were combined, dried (MgSO4) and concentrated to an oil. The oil was purified by silica gel flash column chromatography to give a yield of 40%. $^1H$ NMR ($CDCl_3$) δ 1.44 (t, 6H, 2×$CH_2$), 2.11 (m, 2H, $CH_2$), 3.54 (t, 2H, $CH_2$), 4.23 (t, 2H, $CH_2$), 4.45 (q, 4H, 2×$CH_2$), 7.78 (2, 2H, 2×Ar).

Method B

Sodium hydride (2.8 g, 60% in mineral oil) was added to a stirred solution of 3-azido-1-propanol (5.6 g, 55 nmmol) in THF (120 mL). The stirring was continued for 20 min. A solution of diethyl 4-bromopyridine-2,6-dicarboxylate (15 g, 49 mmol) in THF (120 mL) was added dropwise at room temperature to the above stirred mixture. The resulting reaction mixture was stirred at room temperature for 1.5 hours and poured onto ice water (800 mL). The solution was extracted with ethyl acetate. The combined organic extracts were washed with brine, dried ($Na_2SO_4$), and filtered. The solvent was evaporated under reduced pressure and the residue was purified by flash chromatography on a silica gel column (15 cm×5 cm). Elution with hexanes:ethyl acetate (5:1 and 2:1, v/v) afforded 11.3 g (72%) of the title compound as a pale yellow oil.

TLC: Rf 0.42; hexanes:ethyl acetate; 1:1, v/v; silica gel. $^1H$ NMR ($CDCl_3$) δ 1.44 (t, 6 H, J=7.0 Hz), 2.02–2.18 (m, 2 H), 3.54 (t, 2 H, J=6.0 Hz), 4.22 (t, 2 H, J=6.0 Hz), 4.46 (q, 4 H, J=7.0 Hz), 7.77 (s, 2 H).

Example 56

4-(3-Azidopropoxy)-2,6-dihydroxymethylpyridine

To a stirred solution of Diethyl-4-(3-azidopropoxy)-2,6-pyridinedicarboxylate (4.2 mmol) in dichloromethane (10 mL) and absolute ethanol (15 mL), was added in portions, $NaBH_4$ (4.2 mmol) at 25° C. Powdered $CaCl_2$ (4.2 mmol) was added cautiously in small portions and the evolution of hydrogen was allowed to cease before each further addition. The reaction mixture was stirred for 2 hours. Water (100 mL) was added and the reaction mixture was extracted several times with ethyl acetate. The ethyl acetate layers were combined dried ($MgSO_4$and concentrated in vacuo. The resultant residue was purified by silica gel flash column chromatography to give the title compound. $^1H$ NMR (DMSO) δ 2.00 (m, 2H, $CH_2$), 3.52 (t, 2H, $CH_2$), 4.13 (t, 2H, $CH_2$), 4.45 (d, 4H, 2×$CH_2$), 5.36 (t, 2H, 2×OH), 6.87 (s, 2H, 2×AR Example 57

4-(Azidopropoxy)-2,6-diformyl-pyridine

DMSO (1.21 mL, 17.1 mmol) was diluted with $CH_2Cl_2$ (approximately 25 mL) and cooled to −78° C. Oxalyl chloride (0.745 mL, 8.45 mmol) was added dropwise and the reaction mixture was stirred for 15 minutes. 4-(3-azidopropoxy)-2,6-dihydroxymethylpyridine (1 g, 4.27 mmol) dissolved in $CH_2Cl_2$ (10 mL) was added slowly to the cooled reaction mixture. After 0.5 hour triethylamine (2.77 mL, 19.70 mmol) was added dropwise to the reaction mixture. The dry ice/acetone bath was removed and the reaction mixture was warmed to room temperature for approximately 40 minutes. The reaction mixture was partitioned between $CH_2Cl_2$ and water and extracted several times with $CH_2Cl_2$. The $CH_2Cl_2$ layers were combined, dried (MgSO4) and concentrated in vacuo. The resulting residue was purified by silica gel flash column chromatography to give the title compound. $^1H$ NMR (DMSO) δ 2.02 (m, 2H, $CH_2$), 3.52 (t, 2H, $CH_2$), 4.31 (t, 2H, $CH_2$), 7.64 (s, 2H, 2×Ar), 10.01 (s ,2H, CHO). $^{13}C$ NMR (DMSO) δ 27.61 ($CH_2$), 47.40 ($CH_2$), 66.22 ($CH_2$), 111.58 (Ar), 154.40 (quaternary, Ar), 166,50 (quaternary, Ar), 192.44 (CHO).

Example 58

Library 31, cyclization and formation of new oxime sites

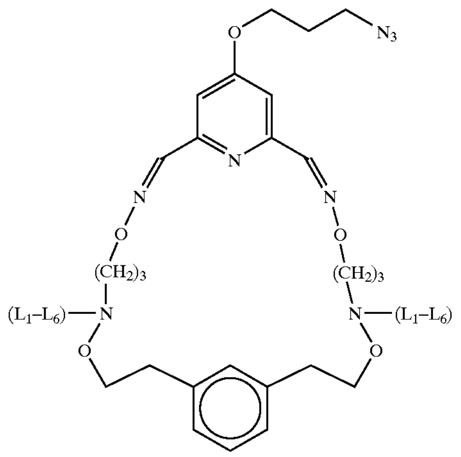

The composition of chemical compounds from Example 53 is treated with N-methyl hydrazine to remove the terminal bis-phthalimido groups. The deprotected material is further treated with 4-(azidopropoxy)-2,6-diformyl-pyridine following the procedures illustrated in Example 52 to give Library 31.

Example 59

Library 32, reduction and functionalization of Library 31

Library 31 is treated with ACOH/$NaCNBH_3$ to reduce the oxime to the hydroxyl amine. The two secondary amine sites thus formed are subsequently treated as per the procedure of Example 32 with a mixture of reactant compounds to give Library 32 having L1–L6 at each amino site.

Example 60

Library 33

Library 32 is treated with triphenyl phosphine at about 80° C. for 12 hours under an atmosphere of argon. The reaction mixture is evaporated to a residue and $NaH_2PO_4$ is added. The mixture is stirred for about 15 minutes and then washed with EtOAc. The aqueous layer is separated and made basic with 3 N NaOH. The resulting mixture is extracted with ether and the combined ether extracts dried over $Na_2SO_4$. The dried ether layer is filtered and concentrated in vacuo to give Library 33.

Example 61

Library 34

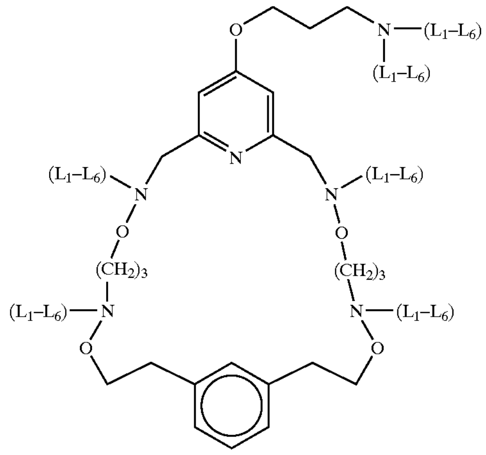

Library 33 is treated with a mixture of reactant compounds as illustrated in Example 32 to give Library 34.

Biological Evaluation

Procedure 1

Antimicrobial Assays

*Staphylococcus aureus*

*Staphylococcus aureus* is known to cause localized skin infections as a result of poor hygiene, minor trauma, psoriasis or eczema. It also causes respiratory infections, pneumonia, toxic shock syndrome and septicemia. It is a common cause of acute food poisoning. It exhibits rapid emergence of drug resistance to penicillin, cephalosporin, vancomycin and nafcillin.

In this assay, the strain *S. aureus* ATCC 25923 (American Type Culture Collection) is used in the bioassay. To initiate the exponential phase of bacterial growth prior to the assay, a sample of bacteria grown overnight at 37° C. in typtocase soy broth (BBL). This bacteria is then used to reinoculate sample wells of 96-well microtiter plates. The assays are carried out in the 96-well microtiter plates in 150 μL volume with approximately $1\times10^6$ cells per well.

Bacteria in typtocase soy broth (75 μL) is added to the compound mixtures in solution in 75 μL water/4% DMSO in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

Procedure 2

Antimicrobial Assays

A. *Streptococcus Pyrogenes*

In this assay, the strain *S. aureus* ATCC 14289 (American Type Culture Collection) is used in the bioassay. To initiate the exponential phase of bacterial growth prior to the assay, a sample of bacteria is grown overnight at 37° C. in 1× Todd-Hewitt broth. This bacteria is then used to reinoculate sample wells of 96-well microtiter plates. The assays are carried out in the 96-well microtiter plates in 150 μL volume with approximately $1\times10^6$ cells per well.

Bacteria in 1× Todd-Hewitt broth (75 μL) is added to the compound mixtures in solution in 75 μL water in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined.

Ampicillin and tetracycline antibiotic positive controls are concurrently tested in each screening assay.

B. *E. coli* imp−

In this assay, the strain *E. coli* imp− obtained from Spenser Bensen (Sampson, B. A., Misra, R. & Benson, S. A. (1989), *Genetics*, 122, 491–501, Identification and characterization of a new gene of *Escherichia coli* K-12 involved in outer membrane permeability) is used. To initiate the exponential phase of bacterial growth prior to the assay, a sample of bacteria is grown overnight at 37° C. in Luria broth. This bacteria is then used to reinoculate sample wells of 96-well microtiter plates. The assays are carried out in the 96-well microtiter plates in 150 μL volume with approximately $1\times10^6$ cells per well.

Bacteria in Luria broth (75 μL) is added to the compound mixtures in solution in 75 μL water in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

Combinatorial libraries in accordance with the present invention have been tested for antibacterial activity utilizing assays that determine the minimum inhibitory concentration (MIC). The antibacterial assays utilize streptococcus pyogenes and escherichia coli imp-. Activity has been detected in a number of libraries of the present invention.

The following data are for first round libraries or parent libraries that were assayed for activity in accordance with the methods illustrated in Procedures 2A and 2B.

| Compounds | *S. pyrogenes* | *E. coli* | |
|---|---|---|---|
| 15–21 | 50–100 μM | 50–100 μM | (Ex. 4) |
| 22–28 | 25–50 μM | 50–100 μM | (Ex. 6) |
| 106–154 | 12.5–25 μM | 25–50 μM | (Ex. 14) |

The minimum inhibitory concentration (MIC) exhibited by a mixture of compounds containing 1-[2'-(N-benzothiazol-2"-yl)amino]ethyl-4-alkaryl piperazine where alkaryl is benzyl, m-methylbenzyl, m-nitrobenzyl, m-fluorobenzyl, m-cyanobenzyl, m-trifluoromethylbenzyl and m-methylcarboxylbenzyl is 50–100 μM for both gram-positive bacteria, *E. Coli* and gram-negative bacteria, *S. Pyogenes*. The MIC exhibited by a mixture of compounds containing 1-[2'-(N-cycloheptyl)amino]ethyl-4-alkaryl piperazine is 50–100 μM for gram-positive bacteria, *E. Coli* and 25–50 μM for gram-negative bacteria, *S. Pyogenes*. The MIC exhibited by a mixture of compounds containing 1-[2'-(N-cycloheptyl-N-alkaryl)amino]ethyl-4-alkaryl piperazine is 25–50 μM for gram-positive bacteria, *E. Coli* and 12.5–25 μM for gram-negative bacteria, *S. Pyogenes.*

Procedure 3

Antfungal Assay

*C. albicans*

In this assay, the strain *C. albicans* ATCC 10231 (American Type Culture Collection) is used in the bioassay. To initiate the exponential phase of yeast growth prior to the assay, a sample of yeast is grown overnight at 37° C. in YM media. This yeast is then used to reinoculate sample wells of 96-well microtiter plates. The assays are carried out in the 96-well microtiter plates in 150 μL volume with approximately $1\times10^6$ cells per well.

Yeast in YM media (75 μL) is added to the compound mixtures in solution in 75 μL water in the individual well of the microtiter plate. Final concentrations of the compound mixtures are 25 μM, 10 μM and 11M. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Amphotericin B positive control is concurrently tested in each screening assay.

Procedure 4

RNA Binding Assay

The effect of libraries on tat/TAR interactions

The effects of combinatorial libraries on tat/TAR, RNA/protein interactions are examined using a rapid and reproducible binding assay. The assay consists of a biotinylated truncated version of the HIV-1 TAR stem-loop, which is anchored to the wells of a 96 well ELISA plate which has been coated with streptavidin. The TAR RNA is recognized by the HIV-1 protein tat and the amount of tat bound is quantitated using an antibody raised against tat and a secondary antibody conjugated to an alkaline phosphatase or HRP enzyme to produce a calorimetric reaction.

Materials:

A 39 residue tat peptide (aa 49–85 of HIV tat protein). This is the C terminal basic binding domain of the tat protein. This peptide was synthesized by a contract lab.

A 30 base RNA oligonucleotide consisting of the bulge and stem/loop structure of HIV TAR which has also been Biotin conjugated. This RNA oligonucleotide was synthesized in house.

A biotinylated HIV RRE RNA oligonucleotide synthesized in house.

Binding buffer: 40 mM Tris-HCl (pH 8.0), 0.01% NP-40, 20% glycerol, 1.5 mM MgCl, 0.01% NaN3, 50 mM KCl.

Streptavidin coated 96 well microtitre plates (Elkay Labsystems).

Protein A/G alkaline phosphatase (Pierce).

Anti tat antiserum (BioDesign).

PNPP substrate (Pierce).

Methods:

To each well of a Streptavidin coated 96 well ELISA plate is added 200 μl of a solution of the 30 base TAR sequence (20 nM) in binding buffer. The plate is incubated at 4° C. for 1 hour. The biotintylated HIV RRE RNA oligonucleotide is bound to selected wells as a negative control RNA. The plate is washed with binding buffer three times and 100 $\mu$l of a 100 nM solution of the 39 residue tat peptide in binding buffer is added to each well. Combinatorial libraries or deconvoluted combinatorial libraries are added to selected wells of the plate at initial concentrations of 100 $\mu$M. The plate is incubated for 1 hour at room temperature.

The plate is washed with binding buffer three times and blocked with binding buffer +5% FCS. 100 $\mu$l of tat antiserum diluted 1:700 in binding buffer is added to the wells of the plate and the plate is incubated for 1.5 hours at 4° C. The plate is washed three times with binding buffer and 150 $\mu$L of a solution of protein A/G alkaline phosphatase diluted 1:5000 in binding buffer is added to each well. The plate is incubated for 1.5 hours at 4° C. followed by washing three times with binding buffer. 150 $\mu$L of PNPP substrate is added to each well and the plate is incubated for 1 hour at 37° C. The absorbance of each well is read in a multiwell plate reader.

Procedure 5

Antimicrobial Mechanistic Assay

Bacterial DNA Gyrase

DNA gyrase is a bacterial enzyme which can introduce negative supercoils into DNA utilizing the energy derived from ATP hydrolysis. This activity is critical during DNA replication and is a well characterized target for antibiotic inhibition of bacterial growth. In this assay, libraries of compounds are screened for inhibition of DNA gyrase. The assay measures the supercoiling of a relaxed plasmid by DNA gyrase as an electrophoretic shift on an agarose gel. Initially all library pools are screened for inhibitory activity at 30 $\mu$M and then a dose response analysis is effected with active subsets. Novobiocin, an antibiotic that binds to the β subunit of DNA gyrase is used as a positive control in the assay. The sensitivity of the DNA gyrase assay was determined by titrating the concentration of the know DNA gyrase inhibitor, Novobiocin, in the supercoiling assay. The $IC_{50}$ was determined to be 8 nM, sufficient to identify the activity of a single active species of comparable activity in a library having 30 $\mu$M concentration.

Procedure 6

Use of a Combinatorial Library for Identifying Metal Chelators and Imaging Agents This procedure is used to identify compounds of the invention from libraries of compounds constructed to include a ring that contains an ultraviolet chromophore. Further the chemical functional groups attached to the compounds of the invention are selected from metal binders, coordinating groups such as amine, hydroxyl and carbonyl groups, and other groups having lone pairs of electrons, such that the compounds of the invention can form coordination complexes with heavy metals and imaging agents. The procedure is used to identify compounds of the invention useful for chelating and removing heavy metals from industrial broths, waste stream eluents, heavy metal poisoning of farm animals and other sources of contaminating heavy metals, and for use in identifying imaging agent carriers, such as carriers for technetium 99.

An aliquot of a test solution having the desired ion or imaging agent at a known concentration is added to an aliquot of standard solution of the pool under assay. The UV spectrum of this aliquot is measured and is compared to the UV spectrum of a further aliquot of the same solution lacking the test ion or imaging agent. A shift in the extinction coefficient is indicative of binding of the metal ion or imaging ion to a compound in the library pool being assayed.

Procedure 7

Assay of Combinatorial Library for $PLA_2$ Inhibitors

A preferred target for assay of combinatorially generated pools of compounds is the phospholipase $A_2$ family. Phospholipases $A_2$ ($PLA_2$) are a family of enzymes that hydrolyze the sn-2 ester linkage of membrane phospholipids resulting in release of a free fatty acid and a lysophospholipid (Dennis, E. A., The Enzymes, Vol. 16, pp. 307–353, Boyer, P. D., ed., Academic Press, New York, 1983). Elevated levels of type II $PLA_2$ are correlated with a number of human inflammatory diseases. The $PLA_2$-catalyzed reaction is the rate-limiting step in the release of a number of pro-in-flammatory mediators. Arachidonic acid, a fatty acid commonly linked at the sn-2 position, serves as a precursor to leukotrienes, prostaglandins, lipoxins and thromboxanes. The lysophospholipid can be a precursor to platelet-activating factor. $PLA_2$ is regulated by pro-inflammatory cytokines and, thus, occupies a central position in the inflammatory cascade (Dennis, ibid.; Glaser et al., *TiPs Reviews* 1992, 14, 92; and Pruzanski et al., *Inflammation* 1992, 16, 451). All mammalian tissues evaluated thus far have exhibited $PLA_2$ activity. At least three different types of $PLA_2$ are found in humans: pancreatic (type I), synovial fluid (type II) and cytosolic. Studies suggest that additional isoenzymes exist. Type I and type II, the secreted forms of $PLA_2$, share strong similarity with phospholipases isolated from the venom of snakes. The $PLA_2$ enzymes are important for normal functions including digestion, cellular membrane re-modeling and repair, and in mediation of the inflammatory response. Both cytosolic and type II enzymes are of interest as therapeutic targets. Increased levels of the type II $PLA_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of $PLA_2$ in promoting the pathophysiology observed in certain chronic inflammatory disorders was the observation that injection of type II $PLA_2$ into the footpad of rats (Vishwanath et al., *Inflammation* 1988, 12, 549) or into the articular space of rabbits (Bomalaski et al., *J. Immunol.* 1991, 146, 3904) produced an inflammatory response. When the protein was denatured before injection, no inflammatory response was produced.

The type II $PLA_2$ enzyme from synovial fluid is a relatively small molecule (about 14 kD) and can be distinguished from type I enzymes (e.g. pancreatic) by the sequence and pattern of its disulfide bonds. Both types of enzymes require calcium for activity. The crystal structures of secreted $PLA_2$ enzymes from venom and pancreatic $PLA_2$, with and without inhibitors, have been reported (Scott et al., *Science* 1990, 250, 1541). Recently, the crystal structure of $PLA_2$ from human synovial fluid has been determined (Wery et al., *Nature* 1991, 352, 79). The structure clarifies the role of calcium and amino acid residues in catalysis. Calcium acts as a Lewis acid to activate the scissile ester carbonyl bond of 1,2-diacylglycerophospholipids and binds to the lipid, and a His-Asp side chain diad acts as a general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged amino-terminal helix is situated above the opening of the hydrophobic cleft. Several lines of evidence suggest that the N-terminal portion is the interfacial binding site (Achari et al., *Cold Spring Harbor Symp. Quant. Biol.* 1987, 52, 441; Cho et al., *J. Biol. Chem.* 1988, 263, 11237; Yang et al., *Biochem. J.* 1989, 262, 855; and Noel et al., *J. Am. Chem. Soc.* 1990, 112, 3704).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. Evidence favoring this hypothesis comes from studies revealing that rapid changes in $PLA_2$ activity occur concurrently with changes in the fluorescence of a membrane probe (Burack et al., *Biochemistry* 1993, 32, 583). This suggests that lipid rearrangement is occurring during the interfacial activation process. $PLA_2$ activity is maximal around the melting temperature of the lipid, where regions of gel and liquid-crystalline lipid coexist. This is also consistent with the sensitivity of $PLA_2$ activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger et al., *FEBS Lett.* 1989, 252, 73). These studies clearly show that $PLA_2$ binds exclusively at the boundary region between liquid and solid phase lipid. While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e. phospholipid above its critical micelle concentration), while low levels of activity are observed on monomeric substrate. As a result, competitive inhibitors of $PLA_2$ either have a high affinity for the active site of the enzyme before it binds to the substrate bilayer or partition into the membrane and compete for the active site with the phospholipid substrate. Although a number of inhibitors appear to show promising inhibition of $PLA_2$ in biochemical assays (Yuan et al., *J. Am. Chem. Soc.* 1987, 109, 8071; Lombardo et al., *J. Biol. Chem.* 1985, 260, 7234; Washburn et al., *J. Biol. Chem.* 1991, 266, 5042; Campbell et al., *J. Chem. Soc., Chem. Commun.* 1988, 1560; and Davidson et al., *Biochem. Biophys. Res. Commun.* 1986, 137, 587), reports describing in vivo activity are limited (Miyake et al., *J. Pharmacol. Exp. Ther.* 1992, 263, 1302).

In one preferred embodiment, compounds of the invention are selected for their potential to interact with, and preferably inhibit, the enzyme $PLA_2$. Thus, compounds of the invention can be used for topical and/or systemic treatment of inflammatory diseases including atopic dermatitis and inflammatory bowel disease. In selecting the functional groups, advantage can be taken of $PLA_2$'s preference for anionic vesicles over zwitterionic vesicles. Preferred compounds of the invention for assay for $PLA_2$ include those having aromatic diversity groups to facilitate binding to the cleft of the $PLA_2$ enzyme (Oinuma et al., *J. Med. Chem.* 1991, 34, 2260; Marki et al., *Agents Actions* 1993, 38, 202; and Tanaka et al., *J. Antibiotics* 1992, 45, 1071). Benzyl and 4-hexylbenzyl groups are preferred aromatic diversity groups. $PLA_2$-directed compounds of the invention can further include hydrophobic functional groups such as tetraethylene glycol groups. Since the $PLA_2$ enzyme has a hydrophobic channel, hydrophobicity is believed to be an important property of inhibitors of the enzyme.

After each round of synthesis as described in the above examples, the resulting libraries or pools of compounds are screened for inhibition of human type II $PLA_2$ enzymatic activity. The assay is effected at the conclusion of each round of synthesis to identify the wining pool from that round of synthesis. Concurrently, the libraries additionally can be screened in other in vitro assays to determine further mechanisms of inhibition.

The pools of the libraries are screened for inhibition of $PLA_2$ in the assay using *E. coli* labeled with $^3$H-oleic acid (Franson et al., *J. Lipid Res.* 1974, 15, 380; and Davidson et al., *J. Biol. Chem.* 1987, 262, 1698) as the substrate. Type II $PLA_2$ (originally isolated from synovial fluid), expressed in a baculovirus system and partially purified, serves as a source of the enzyme. A series of dilutions of each of the library pools is done in water: 10 $\mu$l of each pool is incubated for 5 minutes at room temperature with a mixture of 10 $\mu$l $PLA_2$, 20 $\mu$l 5× $PLA_2$ Buffer (500 mM Tris 7.0–7.5, 5 mM $CaCl_2$), and 50 $\mu$l water. Samples of each pool are run in duplicate. At this point, 10 $\mu$l of $^3$H *E. coli* cells is added. This mixture is incubated at 37° C. for 15 minutes. The enzymatic reaction is stopped with the addition of 50 $\mu$L 2M HCl and 50 $\mu$L fatty-acid-free BSA (20 mg/mL PBS), vortexed for 5 seconds, and centrifuged at high speed for 5 minutes. 165 $\mu$L of each supernate is then put into a scintillation vial containing 6 ml of scintillant (ScintiVerse) and cpms are measured in a Beckman Liquid Scintillation Counter. As a control, a reaction without the combinatorial pool is run alongside the other reactions as well as a baseline reaction containing no compounds of the invention as well as no $PLA_2$ enzyme. CPMs are corrected for by subtracting the baseline from each reaction data point.

Confirmation of the "winners" is made to confirm that a compound of the invention binds to enzyme rather than substrate and that the inhibition by a compound of the invention that is selected is specific for type II $PLA_2$. An assay using $^{14}$C-phosphatidyl ethanolamine ($^{14}$C-PE) as substrate, rather than *E. coli* membrane, is used to insure enzyme rather than substrate specificity. Micelles of $^{14}$C-PE and deoxycholate are incubated with the enzyme and a compound of the invention. $^{14}$C-labeled arachidonic acid released as a result of $PLA_2$-catalyzed hydrolysis is separated from substrate by thin layer chromatography and the radioactive product is quantitated. The "winner" is compared to phosphatidyl ethanolamine, the preferred substrate of human type II $PLA_2$, to confirm its activity. $PLA_2$ from other sources (snake venom, pancreatic, bee venom) and phospholipase C, phospholipase D and lysophospholipase can be used to further confirm that the inhibition is specific for human type II $PLA_2$.

Procedure 8

Probes for the Detection of Specific Proteins and mRNA in Biological Samples

For the reliable, rapid, simultaneous quantification of multiple varieties of proteins or mRNA in a biological sample without the need to purify the protein or mRNA from other cellular components, a protein or mRNA of interest from a suitable biological sample, i.e., a blood borne virus, a bacterial pathogen product in stool, urine and other like biological samples, is identified using standard microbiological techniques. A probe comprising a compound of a combinatorial library of the invention is identified by a combinatorial search as noted in the above examples. Preferred for the protein probe are compounds synthesized to include chemical functional groups that act as hydrogen bond donors and acceptors, sulfhydryl groups, hydrophobic lipophilic moieties capable of hydrophobic interactions groups and groups capable of ionic interactions. The probe is immobilized on insoluble CPG solid support utilizing the procedure of Pon, R. T., Protocols for Oligonucleotides and Analogs, Agrawal, S., Ed., Humana Press, Totowa, N.J., 1993, p 465–496. A known aliquot of the biological sample under investigation is incubated with the insoluble CPG support having the probe thereon for a time sufficient to hybridize the protein or mRNA to the probe and thus form a linkage via the probe to the solid support. This immobilizes the protein or mRNA present in the sample to the CPG support. Other non-immobilized materials and components are then washed off the CPG with a wash media suitable for use with the biological sample. The mRNA on the support is labeled with ethidium bromide, biotin or a commercial radionucleotide and the amount of label immobilized on the CPG support is measured to indicate the amount of mRNA present in the biological sample. In a similar assay a protein is also labeled and quantified.

Procedure 9

Leukotriene $B_4$ Assay

Leukotriene $B_4$ ($LTB_4$) has been implicated in a variety of human inflammatory diseases, and its pharmacological effects are mediated via its interaction with specific surface cell receptors. Library subsets are screened for competitive inhibition of radiolabeled $LTB_4$ binding to a receptor preparation.

A Nenquest™ Drug Discovery System Kit (NEN Research Products, Boston, Mass.) is used to select an inhibitor of the interaction of Leukotriene $B_4$ ($LTB_4$) with receptors on a preparation of guinea pig spleen membrane. [$^3$H] Leukotriene $B_4$ reagent is prepared by adding 5 mL of ligand diluent (phosphate buffer containing NaCl, $MgCl_2$, EDTA and Bacitracin, pH 7.2) to 0.25 mL of the radioligand. The receptor preparation is made by thawing the concentrate, adding 35 mL of ligand diluent and swirling gently in order to re-suspend the receptor homogeneously. Reagents are kept on ice during the course of the experiment, and the remaining portions are stored at −20° C.

Library subsets prepared as per general procedure of examples above are diluted to 5 $\mu$M, 50 $\mu$M and 500 $\mu$M in phosphate buffer (1× PBS, 0.1% azide and 0.1% BSA, pH 7.2), yielding final test concentrations of 0.5 $\mu$M, 5 $\mu$M and 50 $\mu$M, respectively. Samples are assayed in duplicate. [$^3$H] $LTB_4$ (25 $\mu$L) is added to 25 $\mu$L of either appropriately diluted standard (unlabeled $LTB_4$) or library subset. The receptor suspension (0.2 mL) is added to each tube. Samples are incubated at 4° C. for 2 hours. Controls include [$^3$H] $LTB_4$ without receptor suspension (total count vials), and sample of ligand and receptor without library molecules (standard).

After the incubation period, the samples are filtered through GF/B paper that had been previously rinsed with cold saline. The contents of each tube are aspirated onto the filter paper to remove unbound ligand from the membrane preparation, and the tubes washed (2×4 mL) with cold saline. The filter paper is removed from the filtration unit and the filter disks are placed in appropriate vials for scintillation counting. Fluor is added, and the vials shaken and allowed to stand at room temperature for 2 to 3 hours prior to counting. The counts/minute (cpm) obtained for each sample are subtracted from those obtained from the total counts to determine the net cpm for each sample. The degree of inhibition of binding for each library subset is determined relative to the standard (sample of ligand and receptor without library molecules).

Those skilled in the art will appreciate that numerous changes and modifications may be made to the preferred embodiments of the present invention and that such changes and modifications may be made without departing from the spirit of the invention. It is therefore intended that the appended claims cover all such equivalent variations as fall within the true spirit and scope of the invention.

What is claimed is:

1. A method for preparing a chemical library comprising:

reacting a mixture of at least four chemical reactive compounds with at least one scaffold moiety to provide a mixture of reaction products;

transforming said scaffold moiety in said reaction products to alter at least one of its chemical or electrochemical properties and;

reacting said transformed scaffold moiety in said products with a further mixture of at least four chemical reactive compounds to provide said library.

2. The method of claim 1 wherein said transformation comprises the appending to said scaffold of at least one chemical substituient.

3. The method of claim 1 wherein said transformation comprises alteration of the oxidation state of at least one chemical functionality on said scaffold.

4. The method of claim 1 wherein said transformation comprises alkylation of said scaffold.

5. The method of claim 1 wherein said transformation comprises acylation of said scaffold.

6. A method for preparing a chemical library comprising:

reacting a mixture of at least four chemical reactive compounds with at least one scaffold moiety to provide a mixture of reaction products;

transforming said scaffold moiety in said reaction products by effectuating an opening of a chemical ring present in said scaffold; and reacting said transformed scaffold moiety in said products with a further mixture of at least four chemical reactive compounds to provide said library.

7. A method for preparing a chemical library comprising:

reacting a mixture of at least four chemical reactive compounds with a scaffold moiety to provide a mixture of reaction products;

transforming the scaffold moiety portion of said reaction products by cyclicizing a portion of said scaffold; and reacting said transformed reaction products with a set of further chemical reactive species to form said library.

* * * * *

UNITED STATES PATENT AND TRADEMARK OFFICE

CERTIFICATE OF CORRECTION

PATENT NO. : 6,800,444 B1
DATED : October 5, 2004
INVENTOR(S) : Phillip Dan Cook et al.

It is certified that error appears in the above-identified patent and that said Letters Patent is hereby corrected as shown below:

Title Page,
Item [56], References Cited, OTHER PUBLICATIONS, “Debart” reference, delete “Antisens” and insert -- Antisense --;

Column 40,
Line 33, delete “substituient” and insert -- substituent --.

Signed and Sealed this

Ninth Day of May, 2006

JON W. DUDAS
*Director of the United States Patent and Trademark Office*